(12) United States Patent
Emeric et al.

(10) Patent No.: US 9,488,585 B2
(45) Date of Patent: *Nov. 8, 2016

(54) READER DEVICES FOR OPTICAL AND ELECTROCHEMICAL TEST DEVICES

(71) Applicant: Abbott Point of Care Inc., Princeton, NJ (US)

(72) Inventors: Pierre Emeric, Princeton, NJ (US); Graham Davis, Princeton, NJ (US); Thomas Ewart, Toronto (CA); Sergey Gershtein, Skillman, NJ (US)

(73) Assignee: Abbott Point of Care Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/919,377

(22) Filed: Oct. 21, 2015

(65) Prior Publication Data

US 2016/0041104 A1 Feb. 11, 2016

Related U.S. Application Data

(63) Continuation of application No. 13/724,348, filed on Dec. 21, 2012, now Pat. No. 9,194,859.

(60) Provisional application No. 61/579,816, filed on Dec. 23, 2011.

(51) Int. Cl.
*G01N 21/00* (2006.01)
*G01N 21/78* (2006.01)
(Continued)

(52) U.S. Cl.
CPC .............. *G01N 21/78* (2013.01); *G01N 33/48* (2013.01); *G01N 2021/751* (2013.01);
(Continued)

(58) Field of Classification Search
CPC . H01J 37/32935; G01N 21/64; G01N 21/65; G01N 21/68; G01N 2015/1037; G01J 3/02
USPC ....................................................... 356/72–73
See application file for complete search history.

(56) References Cited

U.S. PATENT DOCUMENTS

| 4,509,859 A | 4/1985 | Markart et al. |
| 4,510,383 A | 4/1985 | Ruppender |

(Continued)

FOREIGN PATENT DOCUMENTS

| CN | 101039750 A | 9/2007 |
| EP | 0284232 A1 | 9/1988 |

(Continued)

OTHER PUBLICATIONS

Song et al., "Time-Resolved Luminescent Lateral Flow Assay Technology", Analytica Chimica Acta, vol. 626, No. 2, pp. 186-192, (2008).

(Continued)

*Primary Examiner* — Abdullahi Nur
(74) *Attorney, Agent, or Firm* — Kilpatrick Townsend & Stockton LLP

(57) ABSTRACT

This invention relates generally to devices and methods for performing optical and electrochemical assays and, more particularly, to devices having optical and electrochemical detectors and to methods of performing optical and electrochemical assays using such devices. The present invention is particularly useful for performing immunoassays and/or electrochemical assays at the point-of-care.

12 Claims, 29 Drawing Sheets

(51) Int. Cl.
    *G01N 33/48*     (2006.01)
    *G01N 35/00*     (2006.01)
    *G01N 21/75*     (2006.01)
    *G01N 21/77*     (2006.01)
(52) U.S. Cl.
    CPC . *G01N 2021/752* (2013.01); *G01N 2021/757* (2013.01); *G01N 2021/7763* (2013.01); *G01N 2035/00752* (2013.01)

(56) References Cited

U.S. PATENT DOCUMENTS

| | | | |
|---|---|---|---|
| 4,592,893 | A | 6/1986 | Poppe et al. |
| 5,073,484 | A | 12/1991 | Swanson et al. |
| 5,096,669 | A | 3/1992 | Lauks et al. |
| 5,141,850 | A | 8/1992 | Cole et al. |
| 5,160,701 | A | 11/1992 | Brown, III et al. |
| 5,200,051 | A | 4/1993 | Cozzette et al. |
| 5,201,851 | A | 4/1993 | Holmstrom |
| 5,408,535 | A | 4/1995 | Howard, III et al. |
| 5,415,994 | A | 5/1995 | Imrich et al. |
| 5,447,440 | A | 9/1995 | Davis et al. |
| 5,451,504 | A | 9/1995 | Fitzpatrick et al. |
| 5,559,041 | A | 9/1996 | Kang et al. |
| 5,569,608 | A | 10/1996 | Sommer |
| 5,628,961 | A | 5/1997 | Davis et al. |
| 5,821,399 | A | 10/1998 | Zelin |
| 5,837,546 | A | 11/1998 | Allen et al. |
| 5,989,917 | A | 11/1999 | McAleer et al. |
| 6,642,054 | B2 | 11/2003 | Schermer et al. |
| 6,770,487 | B2 | 8/2004 | Crosby |
| 6,814,844 | B2 | 11/2004 | Bhullar et al. |
| 7,267,799 | B1 | 9/2007 | Borich et al. |
| 7,419,821 | B2 | 9/2008 | Davis et al. |
| 7,763,454 | B2 | 7/2010 | Nazareth et al. |
| 7,780,827 | B1 | 8/2010 | Bhullar et al. |
| 8,017,382 | B2 | 9/2011 | Davis et al. |
| 9,194,859 | B2 * | 11/2015 | Emeric ............ G01N 33/48 |
| 2004/0028566 | A1 | 2/2004 | Ko et al. |
| 2004/0175296 | A1 | 9/2004 | Opalsky et al. |
| 2004/0200721 | A1 | 10/2004 | Bhullar et al. |
| 2005/0009101 | A1 | 1/2005 | Blackburn |
| 2007/0092977 | A1 | 4/2007 | Reich |
| 2007/0099249 | A1 | 5/2007 | Abbott et al. |
| 2007/0121113 | A1 | 5/2007 | Cohen et al. |
| 2007/0202542 | A1 | 8/2007 | Babu et al. |
| 2008/0280285 | A1 | 11/2008 | Chen et al. |
| 2008/0314882 | A1 | 12/2008 | Bhullar et al. |
| 2009/0136922 | A1 | 5/2009 | Barlag et al. |
| 2009/0314946 | A1 | 12/2009 | Song et al. |
| 2010/0032321 | A1 | 2/2010 | Kim et al. |
| 2010/0167294 | A1 | 7/2010 | Huang et al. |
| 2010/0240149 | A1 | 9/2010 | Nazareth et al. |
| 2010/0274155 | A1 | 10/2010 | Battrell et al. |
| 2010/0285082 | A1 | 11/2010 | Fernandez |
| 2011/0150705 | A1 | 6/2011 | Doyle et al. |
| 2012/0121464 | A1 | 5/2012 | Nogami et al. |

FOREIGN PATENT DOCUMENTS

| | | |
|---|---|---|
| EP | 0505636 A1 | 9/1992 |
| EP | 1225442 A2 | 7/2002 |
| EP | 1359419 A1 | 11/2003 |
| WO | WO 88/08534 A1 | 11/1988 |
| WO | WO 91/12336 A1 | 8/1991 |
| WO | WO 2008/076395 A2 | 6/2008 |
| WO | WO 2010/017299 A2 | 2/2010 |
| WO | WO 2010/017299 A3 | 2/2010 |
| WO | WO 2011/095793 A1 | 8/2011 |

OTHER PUBLICATIONS

Novo et al., "Microspot-based ELISA in Microfluidics; Chemiluminescence and colorimetry detection using integrated thin-film hydrogenated amorphous silicon photodiodes", Lab on a Chip, 2011, vol. 11, pp. 4063-4071.

Final Office Action for U.S. Appl. No. 13/724,363 dated Jun. 19, 2014.

Chinese Office Action mailed on Jul. 2, 2015 for CN Patent Application No. 201280068224.5, with English translation, 12 pages.

Final Office Action mailed on Aug. 12, 2015 for U.S. Appl. No. 13/724,363, 17 pages.

International Search Report and Written Opinion mailed May 3, 2013 in corresponding International Application No. PCT/US2012/071307.

Office Action for U.S. Appl. No. 13/724,370 dated Sep. 5, 2014.

* cited by examiner

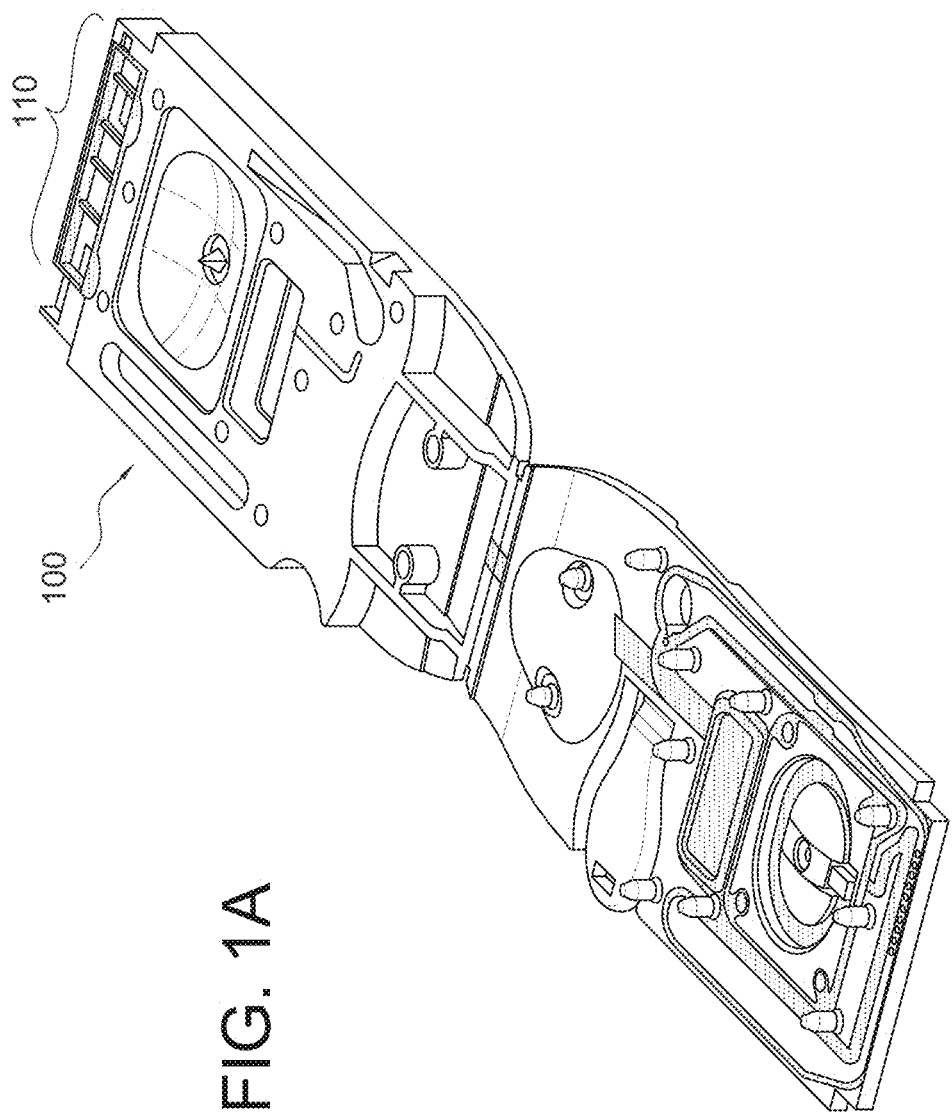

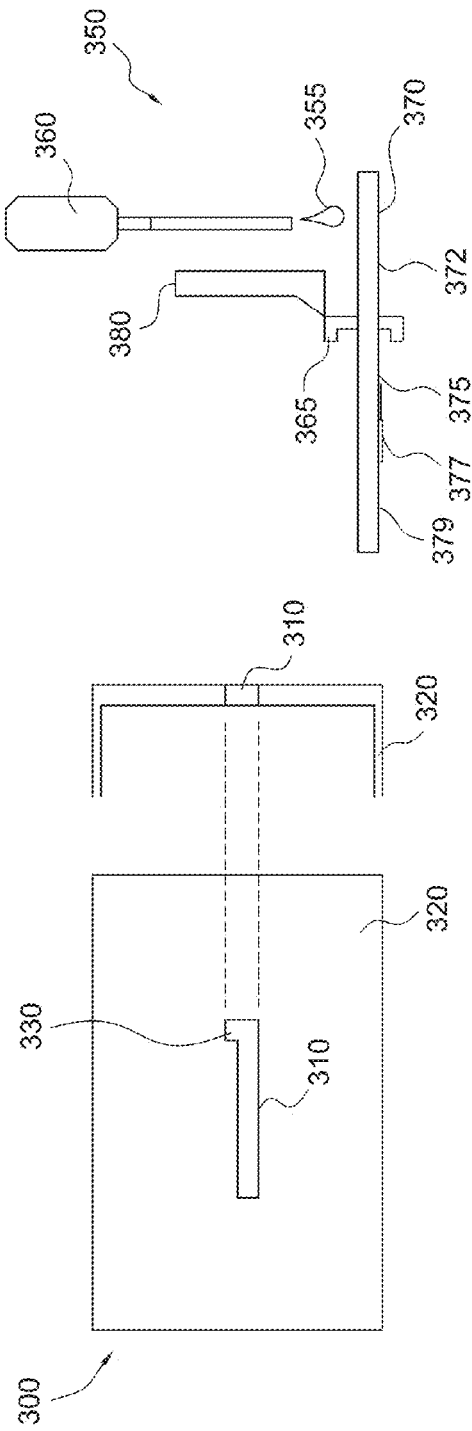
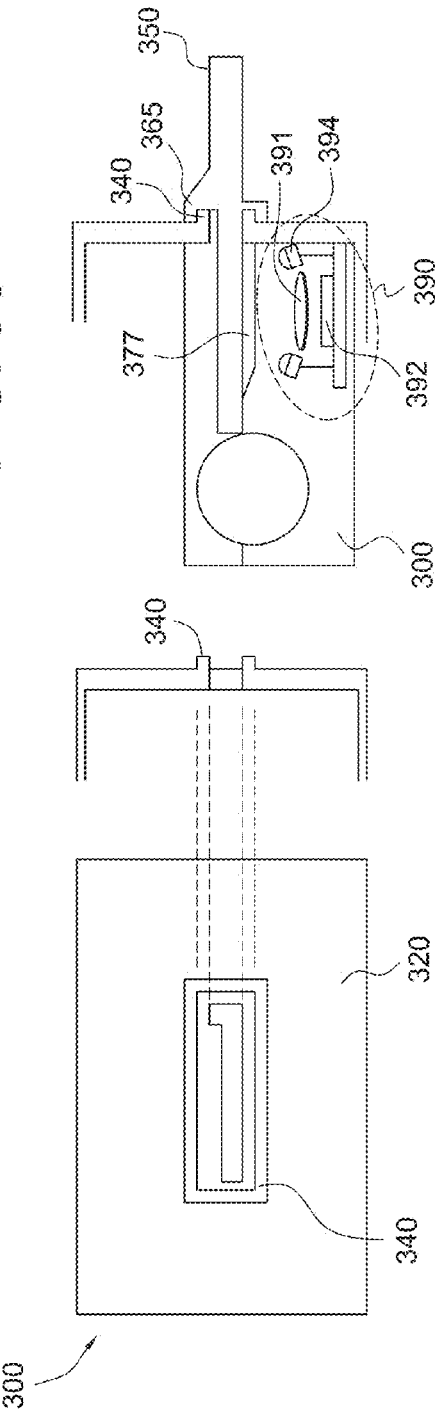
FIG. 3A
FIG. 3B
FIG. 3C
FIG. 3D

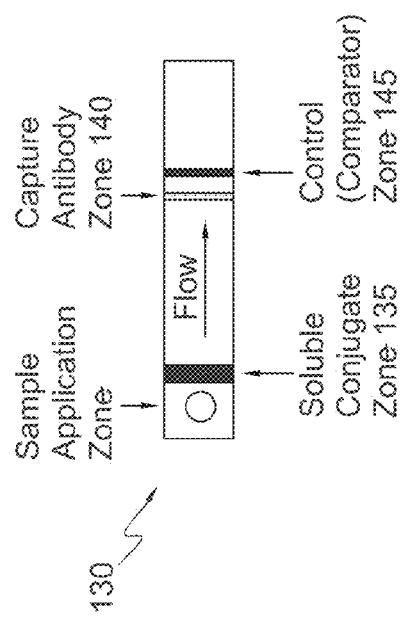
FIG. 7
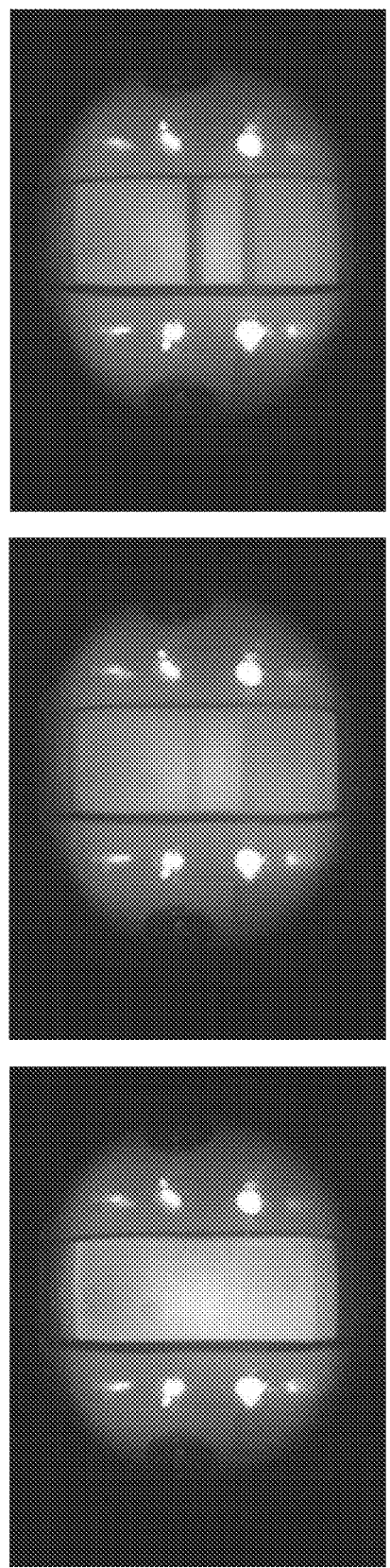
FIG. 8A
FIG. 8B
FIG. 8C

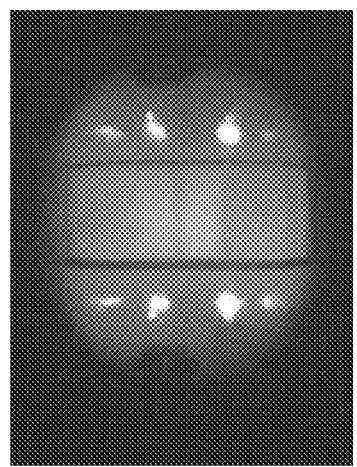
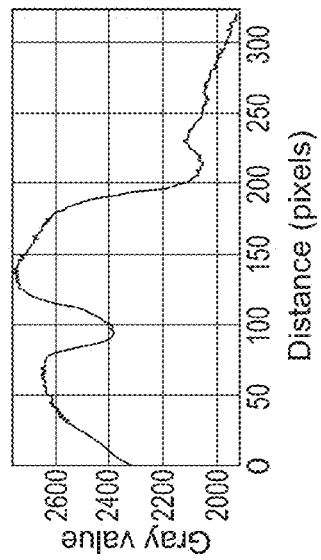
FIG. 11A
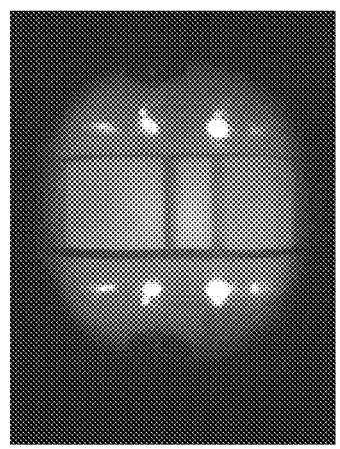
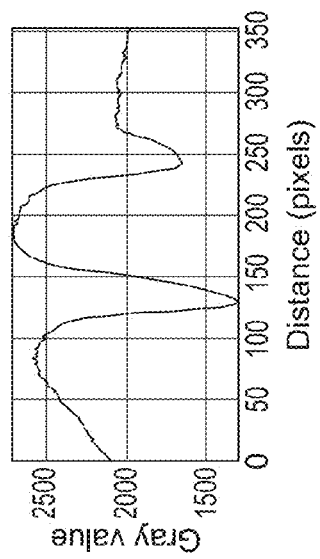
FIG. 11B
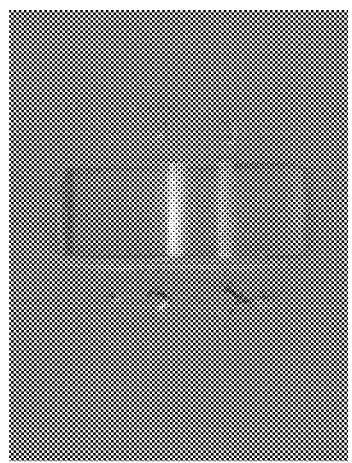
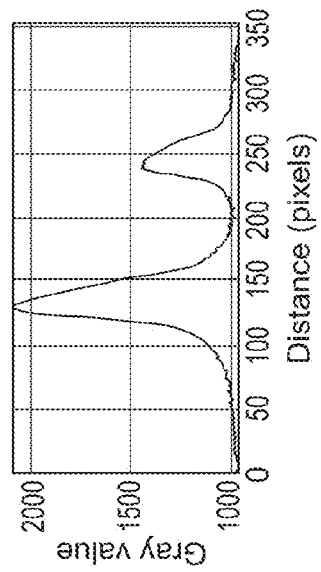
FIG. 11C

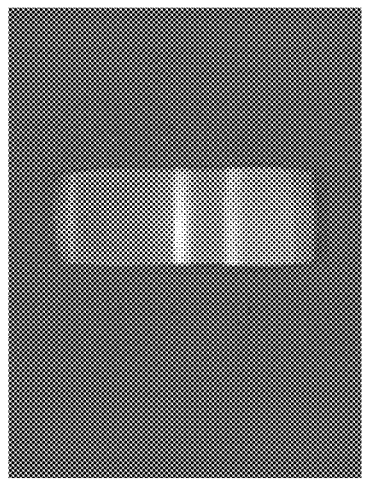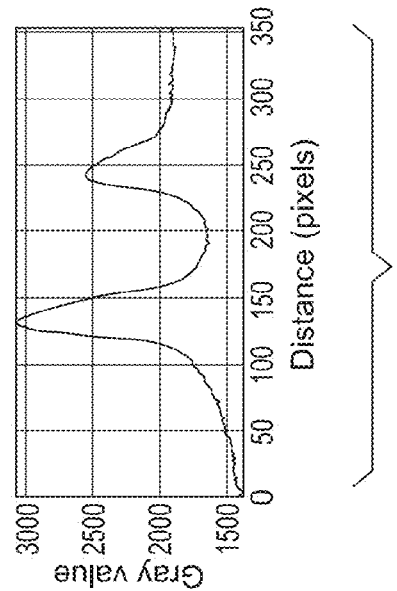
FIG. 12C
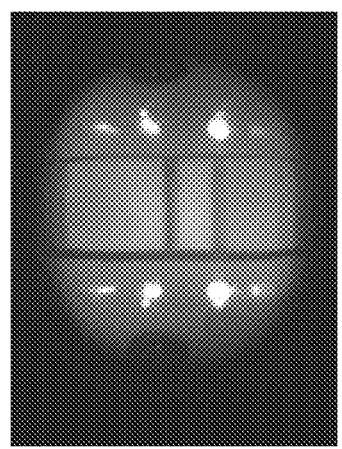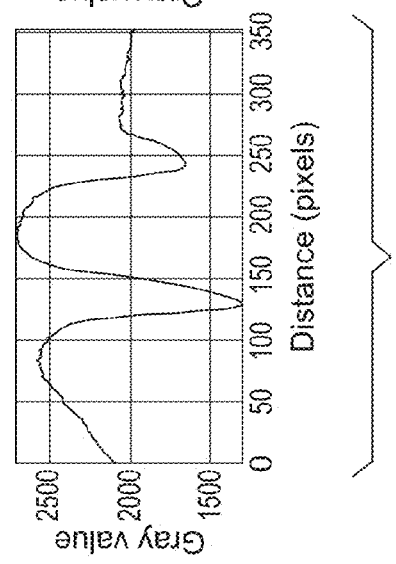
FIG. 12B
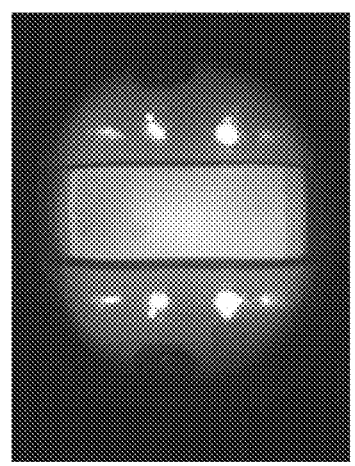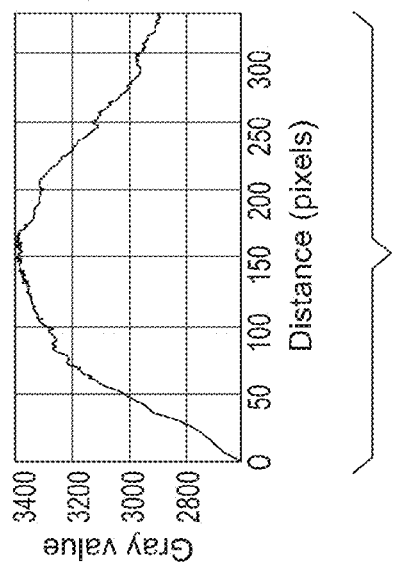
FIG. 12A

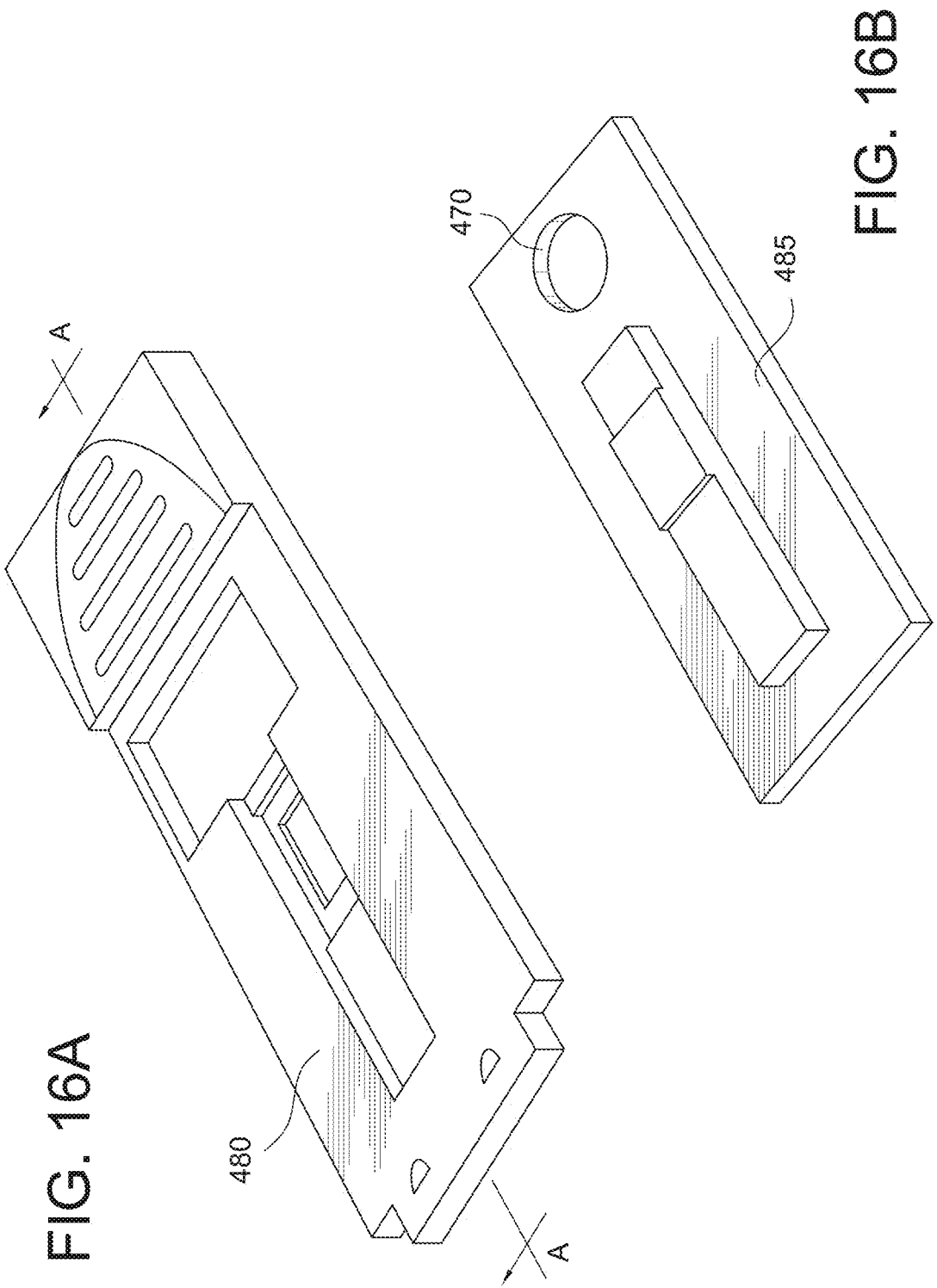

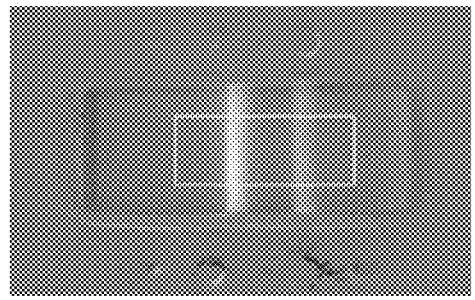
FIG. 28A
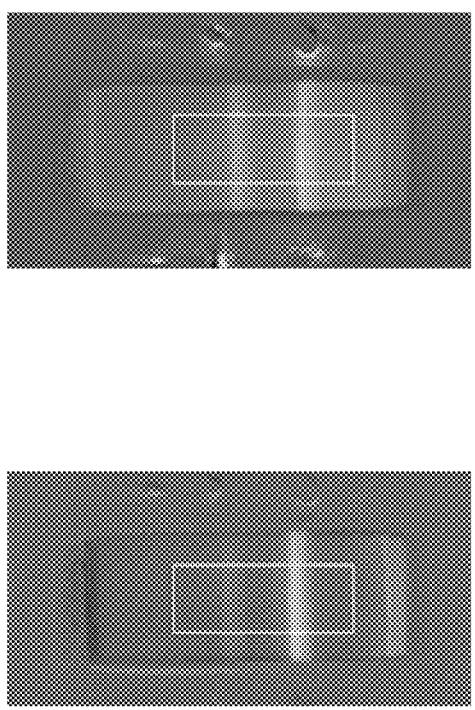
FIG. 28B
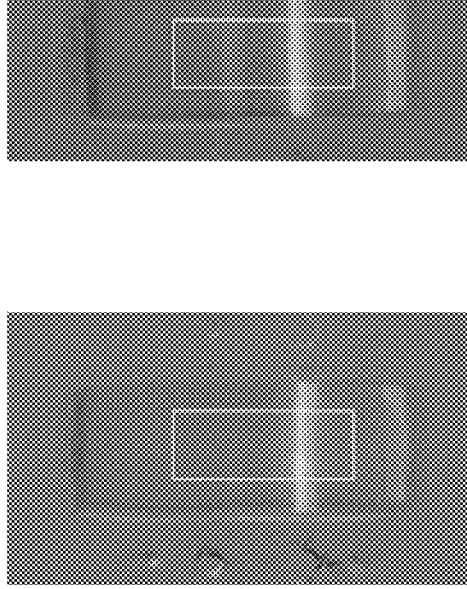
FIG. 28C
FIG. 28D
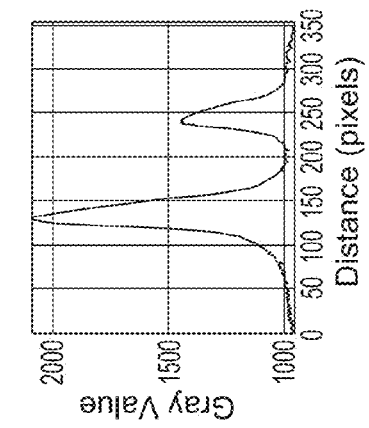
FIG. 29A
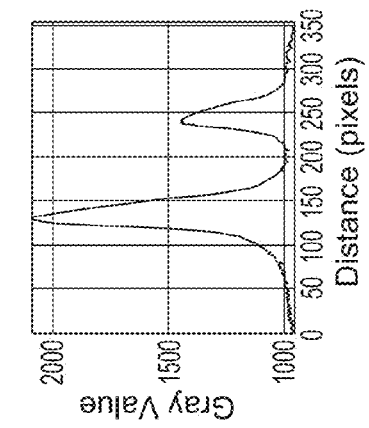
FIG. 29B
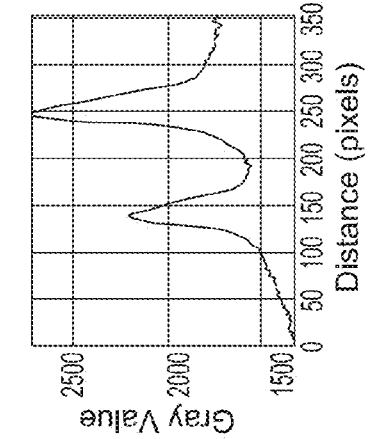
FIG. 29C
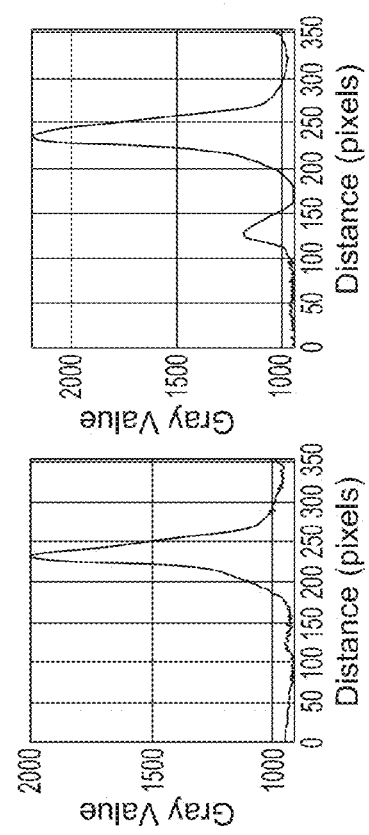
FIG. 29D

READER DEVICES FOR OPTICAL AND ELECTROCHEMICAL TEST DEVICES

CROSS REFERENCE TO RELATED APPLICATIONS

This application is a continuation application of U.S. patent application Ser. No. 13/724,348, filed Dec. 21, 2012, which claims priority to U.S. Provisional Application No. 61/579,816, filed on Dec. 23, 2011, the entire contents of which are hereby incorporated herein by reference.

FIELD OF THE INVENTION

This invention relates generally to devices and methods for performing optical and electrochemical assays and, more particularly, to devices with an optical detector and an electrochemical detector and methods of performing optical and electrochemical assays using such devices.

BACKGROUND OF THE INVENTION

A multitude of laboratory tests for analytes of interest are performed on biological samples for diagnosis, screening, disease staging, forensic analysis, pregnancy testing, drug testing, and other reasons. While a few qualitative tests have been reduced to simple kits for the patient's home use, the majority of quantitative tests still require the expertise of trained technicians in a laboratory setting using sophisticated instruments. Laboratory testing increases the cost of analysis and delays the results. In many circumstances, delay can be detrimental to a patient's condition or prognosis. In these critical situations and others, it would be advantageous to be able to perform such analyses at the point of care, accurately, inexpensively, and with a minimum of delay.

Devices capable of performing such analyses include a disposable sensing device for measuring analytes in a sample of blood, which is disclosed by Lauks et al. in U.S. Pat. No. 5,096,669. Other related devices are disclosed by Davis et al. in U.S. Pat. Nos. 5,628,961 and 5,447,440 for a clotting time. The disclosed devices comprise a reading apparatus and a cartridge that fits into the reading apparatus for measuring analyte concentrations and viscosity changes in a sample of blood as a function of time. However, a potential problem with such disposable devices is variability of fluid test parameters from cartridge to cartridge due to manufacturing tolerances or machine wear. Methods to overcome this potential problem using automatic flow compensation controlled by a reading apparatus using conductimetric sensors located within the cartridge are disclosed by Zelin in U.S. Pat. No. 5,821,399. U.S. Pat. Nos. 5,096,669, 5,628,961, 5,447,440, and 5,821,399 are hereby incorporated in their respective entireties by reference.

Antibodies are extensively used in the analysis of biological analytes. A variety of different analytical approaches have been employed to detect, either directly or indirectly, the binding of an antibody to its analyte. Various alternative assay formats (other than those used in typical research laboratories, such as Western blotting) have been adopted for quantitative immunoassays, which are distinguished from qualitative immunoassay kits, such as pregnancy testing kits. As an example of antibody use, Swanson et al., U.S. Pat. No. 5,073,484, disclose a method in which a fluid-permeable solid medium has reaction zones through which a sample flows. A reactant that is capable of reacting with the analyte is bound to the solid medium in a zone.

However, most of the methods currently available for quantitative immunoassays either are operated manually or require bulky machinery with complex fluidics because the quantitative immunoassays typically require multiple steps (e.g., a binding step followed by a rinse step with a solution that may or may not contain a second reagent). An example of the latter approach is provided in Holmstrom, U.S. Pat. No. 5,201,851, which discloses methods providing complex fluidics for very small volumes on a planar surface. Additionally, photomultipliers, phototransistors and photodiodes have been discussed in the context of immunoassay development. See, e.g., jointly owned Davis et al., U.S. Pat. No. 8,017,382, the entirety of which is incorporated herein by reference.

Microfabrication techniques (e.g. photolithography and plasma deposition) are known for construction of multilayered sensor structures in confined spaces, e.g., the confined spaces of cartridges for the above-disclosed devices. Methods for microfabrication of electrochemical immunosensors, for example on silicon substrates, are disclosed by Cozzette et al. in U.S. Pat. No. 5,200,051, the entirety of which is incorporated herein by reference. These include dispensing methods, methods for attaching biological reagent, e.g., antibodies, to surfaces including photoformed layers and microparticle latexes, and methods for performing electrochemical assays.

Additionally, jointly owned Davis et al., U.S. Pat. No. 7,419,821, the entirety of which is incorporated herein by reference, discloses a single-use cartridge designed to be adaptable to a variety of real-time assay protocols, preferably assays for the determination of analytes in biological samples using immunosensors or other ligand/ligand receptor-based biosensor embodiments. The cartridge provides features for processing a metered portion of a sample, for precise and flexible control of the movement of a sample or second fluid within the cartridge, for the amending of solutions with additional compounds during an assay, and for the construction of immunosensors capable of adaptation to diverse analyte measurements.

Furthermore, Davis et al., U.S. Pat. No. 7,419,821, discloses mobile microparticles capable of interacting with an analyte and ways of localizing the microparticles onto a sensor, e.g., with a magnetic field or a porous filter element. However, to date, one step immunoassays with limited or no wash steps have not been used for antigens where the presence of endogenous related antigens create high backgrounds that confound detection results. This is particularly true when the endogenous antigens are found at high molar concentrations in excess of the antigen of interest, which is common for some disease conditions.

Immunoassays for the determination of analytes in biological samples, as discussed above, may include a variety of assay types such as lateral flow tests. Typical lateral flow tests are a type of immunoassay in which the test sample flows along a solid substrate via capillary action. For example, once the test sample is applied to the substrate, the sample may traverse the substrate via capillary action encountering a colored reagent, which mixes with the sample, and subsequently to test lines or zones that have been pretreated with an antibody or antigen. The colored reagent can become bound at the test lines or zones depending upon the presence or absence of the analyte in the test sample. General background for lateral flow technology may be found in the following: (i) Brown et al., U.S. Pat. No. 5,160,701, disclose a solid-phase analytical device and method; (ii) Cole et al., U.S. Pat. No. 5,141,850, disclose a porous strip for an assay device; (iii) Fan et al., WO 91/012336, disclose an immunochromatographic assay and method; (iv) Fitzpatrick et al., U.S. Pat. No. 5,451,504, disclose a method and device for detecting the presence of analyte in a sample; (v) Imrich et al., U.S. Pat. No. 5,415,994, disclose a lateral flow medical diagnostic assay device; (vi) Kang et al., U.S. Pat. No. 5,559,041, disclose immunoassay devices and materials; (vii) Koike, EP 0505636, discloses immunochromatographic assay methods; (viii) May et al., WO 88/008534, disclose various immunoassay devices; (ix) Rosenstein, EP 0284232, discloses details of solid phase assays; (x) Sommer, U.S. Pat. No. 5,569,608, discloses quantitative detection of analytes on immunochromatographic strips; and (xi) Allen et al., U.S. Pat. No. 5,837,546, disclose electronic assay devices and methods.

Lateral flow test devices have also been combined with barcode systems for the determination of information pertinent to the lateral flow test, e.g., the identification of the analyte being tested and the patient. General background for the use of barcodes on lateral flow and other types of devices for testing clinical samples may be found in the following: (i) Markart et al., U.S. Pat. No. 4,509,859; (ii) Poppe et al., U.S. Pat. No. 4,592,893; (iii) Ruppender, U.S. Pat. No. 4,510,383; (iv) Crosby, U.S. Pat. No. 6,770,487; (v) commercial items, e.g., Ektachem™ and Reflotron™ products; (vi) Piasio et al., WO 2010017299; (vii) Broich et al., U.S. Pat. No. 7,267,799; (viii) Bhullar et al., U.S. Pat. No. 6,814,844 and McAleer et al. U.S. Pat. No. 5,989,917; (ix) Rehm, EP 1225442; (x) Eyster et al., EP 1359419, and (xi) Howard, III et al., U.S. Pat. No. 5,408,535; (xii) Babu et al., U.S. Patent Application Publication No. 2007/0202542; and (xiii) Nazareth et al., U.S. Pat. No. 7,763,454, and (ixx) Nazareth et al., U.S. Patent Application Publication No. 2010/0240149.

Lateral flow assays also have been adapted to include time-resolved luminescence detection. Time-resolved luminescence detection techniques may have higher detection sensitivity than conventional luminescence techniques (e.g., fluorescence and phosphorescence) due to higher signal-to-noise ratios. Compared with standard luminescence detection methods that separate the luminescence of interest from the background signal through wavelength differences, time-resolved luminescence techniques separate the luminescence of interest from the background signal through lifetime differences. Time-resolved luminescence techniques operate by exciting a luminescent label of a long luminescence lifetime with a short pulse of light, and waiting a brief period of time (e.g., 10 µs) for the background and other unwanted light to decay to a low level before collecting the remaining long-lived luminescence signal. General background for lateral flow assays capable of time-resolved luminescence detection may be found in the following: Song and M. Knotts, "Time-Resolved Luminescent Lateral Flow Assay Technology," Analytica Chimica Acta, vol. 626, no. 2, pp. 186-192, (2008), and Song et al. U.S. Patent Application Publication No. 2009/0314946.

As an alternative to the lateral flow test formats, immunoassays may also include microarray techniques, which rely on optical detection. Microarrays are an array of very small samples of purified DNA or protein target material arranged typically as a grid of hundreds or thousands of small spots on a substrate. When the microarray is exposed to selected probe material, the probe material selectively binds to the target spots only where complementary bonding sites occur. Subsequent scanning of the microarray by a scanning instrument may be used to produce a pixel map of fluorescent intensities, which can be analyzed for quantification of fluorescent probes and hence the concentration of an analyte. General background for microarray techniques may be found, for example, in Schermer et al., U.S. Pat. No. 6,642,054, which discloses microarray spotting instrumentation that incorporates sensors for improving the performance of microarrays.

Therefore, there exists within the field of analyte sensing, and in particular for applications in which analytes must be determined within biological samples such as blood, a need for devices that can rapidly and simply determine the presence and/or concentration of analytes at patient point-of-care, and can be performed by less highly trained staff than is possible for conventional laboratory-based testing. It would, for example, be of benefit in the diagnosis and treatment of critical medical conditions for the attending physician or nurse to be able to obtain clinical test results without delay. The need also exists for improved devices that are adaptable to the determination of a range of analytes.

SUMMARY OF THE INVENTION

The invention is directed to reader devices for reading optical or electrochemical test cartridges. In one embodiment, the reader device comprises a housing including a cartridge receiving port configured to receive the optical or electrochemical test cartridge. The reader device also includes an optical sensor within the port configured to read a first signal from an optical feature of an optical test cartridge. The reader device also includes an electrical connector within the port configured to mate with one or more electrodes of an electrochemical test cartridge and receive a second signal therefrom. The reader device is preferably configured to provide a qualitative, semi-quantitative, or quantitative analysis display based on either or both the first signal and/or said second signal.

The reader preferably includes a processor configured to provide said display based on either or both said first signal and/or said second signal. The reader optionally further comprises at least one locating means configured to position said optical or electrochemical test cartridge in said housing with respect to said optical sensor or said electrical connector.

In one aspect the reader includes a lip surrounding said port and configured to engage with a light baffle on said optical test cartridge. The optical sensor optionally comprises an optical imager, and the optical feature may comprise an optical assay. The optical imager is preferably configured to image said optical assay of the optical test cartridge. The optical assay may comprise a qualitative or semi-quantitative lateral flow test. The optical imager may be further configured to image a code of the optical test cartridge, e.g., a one- or two-dimensional barcode comprising information. The optical imager may be further configured to obtain and transmit the information to the processor. The processor is preferably configured to display the information with the display obtained from either or both said first signal and/or said second signal. The optical sensor may further comprise a light source configured to illuminate said optical assay and said two-dimensional barcode. For example, the light source may comprise a first light-emitting diode configured to illuminate said optical assay and a second light-emitting diode configured to illuminate said two-dimensional barcode. The optical imager optionally is further configured to image the two-dimensional barcode and the optical assay sequentially or simultaneously.

The optical test cartridge may, for example, be a qualitative or semi-quantitative lateral flow test device or a combined qualitative or semi-quantitative lateral flow test device and quantitative non-lateral flow test device. The optical test cartridge optionally comprises a testing system operable to detect an analyte selected from the group consisting of hCG and drugs of abuse. The optical test cartridge may comprise a testing system operable to detect a predetermined analyte in a biological sample selected from the group consisting of: urine, blood, plasma, serum, and amended forms thereof.

In one aspect, the electrochemical test cartridge is a quantitative non-lateral flow test device or a combined qualitative or semi-quantitative lateral flow test device and quantitative non-lateral flow test device. For example, the electrochemical test cartridge may comprise a testing system operable to detect an analyte selected from the group consisting of: hCG, K, Na, Cl, Ca, Mg, pH, pO2, pCO2, glucose, urea, creatinine, lactate, CKMB, TnI, TnT, BNP, NTproBNP, proBNP, TSH, D-dimer, PSA, PTH, NGAL, galectin-3, AST, ALT, albumin, phosphate and ALP. The electrochemical test cartridge preferably comprises a testing system operable to detect a predetermined analyte in a biological sample selected from the group consisting of: urine, blood, plasma, serum, and amended forms thereof.

In another embodiment, the invention is to an instrument comprising a housing including a cartridge receiving port configured to receive a plurality of testing cartridges, wherein said plurality of testing cartridges comprises at least two selected from the group consisting of: a qualitative or semi-quantitative lateral flow test device; a quantitative non-lateral flow test device; and a combined qualitative or semi-quantitative lateral flow test device and a quantitative non-lateral flow test device.

In another embodiment, the invention is to an analyte testing system comprising: an instrument including a housing with a cartridge receiving port; and a plurality of testing cartridges including at least two selected from the group consisting of: a qualitative or semi-quantitative lateral flow test device; a quantitative non-lateral flow test device; and a combined qualitative or semi-quantitative lateral flow test device and a quantitative non-lateral flow test device. The cartridge receiving port is configured to receive said plurality of testing cartridges.

In another embodiment, the invention is to an instrument for receiving a biological sample test cartridge, the instrument comprising: a connector configured to engage with electrical contacts on a first test cartridge; and an imager configured to image a detection zone on a lateral flow test strip on said first test cartridge or a second test cartridge.

In another embodiment, the invention is to an instrument for sequentially receiving a plurality of cartridges, the instrument comprising: a universal port configured to receive a series of at least two single-use test cartridges selected from the group consisting of: optical test cartridge, electrochemical test cartridge, and opto-electrochemical test cartridge; an electrical connector positioned in said universal port and configured to mate electrically with said electrochemical and said opto-electochemical test cartridges; and an optical imager positioned in said universal port and configured to read said optical and said opto-electrochemical test cartridges.

In another embodiment, the invention is to an instrument for receiving at least two types of pregnancy test cartridges, the instrument comprising: a housing with a cartridge receiving port that is configured to receive the at least two types of pregnancy test cartridges, wherein said at least two types of pregnancy test cartridges comprise a qualitative or semi-quantitative lateral flow hCG test device and a quantitative non-lateral flow hCG test device.

BRIEF DESCRIPTION OF THE DRAWINGS

The present invention will be better understood in view of the following non-limiting figures.

FIG. 1A shows a top perspective view of an electrochemical cartridge in an open position prior to being folded;

FIGS. 3A-3D show an instrument port for accepting and reading optical and electrochemical test devices;

FIG. 7 shows a conceptual representation of a lateral flow test strip;

FIGS. 8A-8C show images of lateral flow assay strips at various stages of testing;

FIGS. 11A-11C show processing of images and signals resulting in a difference image and signal in accordance with some embodiments of the invention;

FIGS. 12A-12C show processing of images and signals resulting in a difference image and signal in accordance with alternative or additional embodiments of the invention;

FIGS. 16A-16C show top and bottom perspective views and a side view, respectively, of an optical cartridge in accordance with some embodiments of the invention;

FIGS. 28A-28D show processed images of experiments conducted at various concentrations; and FIGS. 29A-29D show processed signals for experiments conducted at various concentrations.

DETAILED DESCRIPTION OF THE INVENTION

Introduction

The present invention relates to reader devices that are operable with optical and/or electrochemical assay systems and to novel cartridges for use with such reader devices. More particularly, the present invention relates to immunoassays, and devices and methods for performing immunoassays and/or electrochemical assays, preferably in the point-of-care setting. The present invention advantageously provides accurate optical and/or electrochemical test results using a single point-of-care reader device.

In one embodiment, the invention is to a reader device having a cartridge receiving port configured to accept multiple cartridge types, such as an optical cartridge and/or an electrochemical assay cartridge. In another embodiment, the invention is to a cartridge comprising optical and electrochemical assay systems. In further embodiments, the invention is to a cartridge for optical detection of the results of a lateral flow test, e.g., in a qualitative (e.g., providing a positive or negative test result), semi-quantitative manner (e.g., wherein the darkness of an optical signal correlates to approximate analyte concentration), or quantitative manner. In another embodiment, the invention is to a cartridge for optical detection of the results of a microarray. In accordance with some aspects of invention, the cartridge may be further provided with an integrated means for sample actuation. The cartridge may also be provided with an integrated test sample separator.

FIG. 1A shows an exemplary cartridge 100, e.g., an i-STAT™ cartridge sold by Abbott Point of Care Inc., Princeton, N.J., USA, that may be employed with the reader devices of the present invention. Jointly owned Doyle et al., U.S. Patent Application Publication No. 2011/0150705, the entirety of which is incorporated herein by reference, provides a discussion of the structural features of the cartridge 100. Specifically, the cartridge 100 comprises an electrochemical assay system 110 including electrochemical sensors. In some embodiments of the present invention, the cartridge 100 may be modified either to replace the electrochemical assay system 110 with an optical assay system or to include the optical assay system along with the electrochemical assay system 110.

Figure 1B:
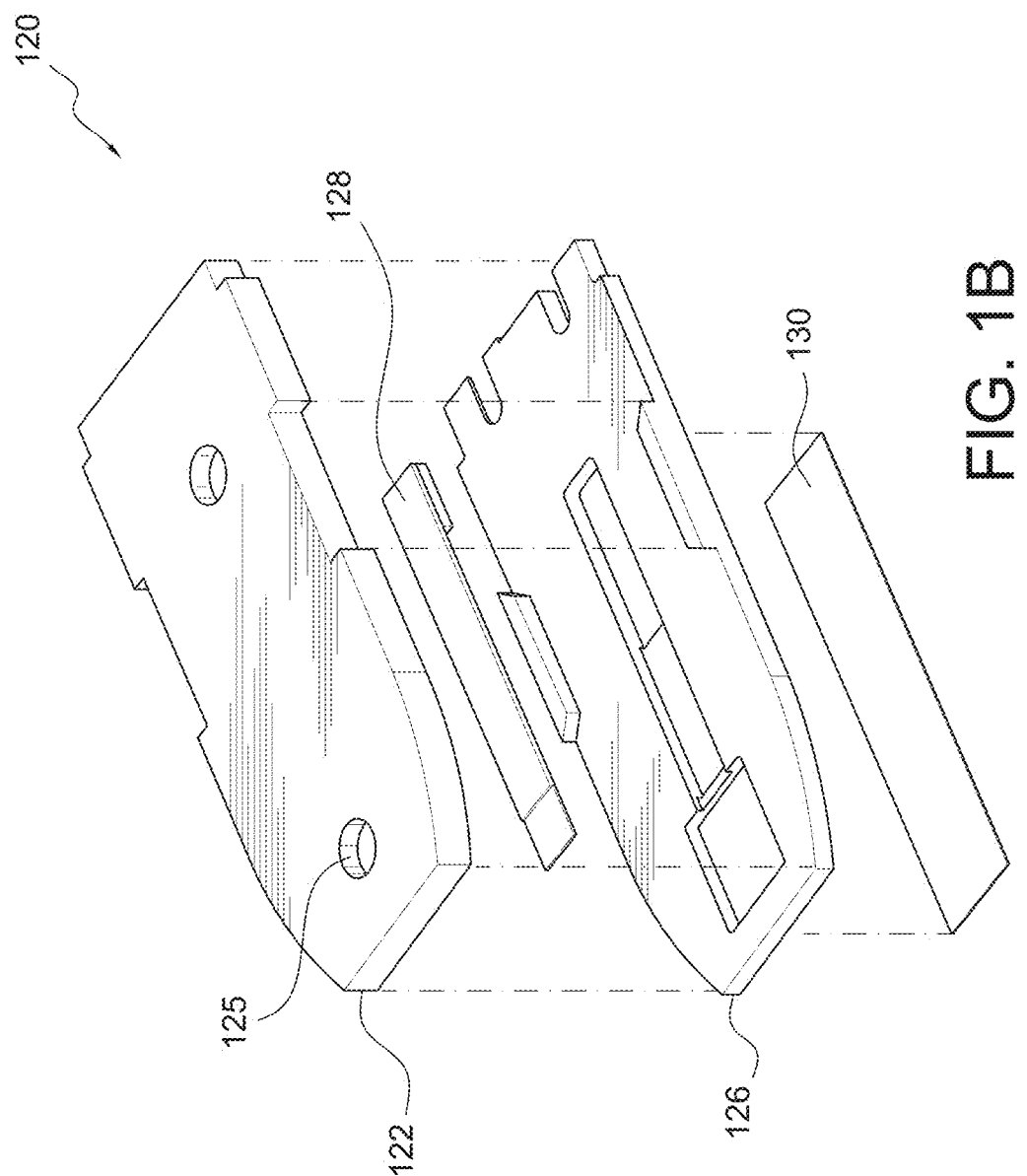
FIG. 1B shows a top perspective view of an optical cartridge in an open position prior to being folded.

For example, FIG. 1B provides an exemplary cartridge 120 comprising an optical assay system in accordance with some embodiments of the invention. Specifically, the cartridge 120 may include a cover 122 with a sample input port 125, a base 126 that supports a lateral flow test strip 128, and an optional transparent tape or film 130 that covers an optical test window in the base 126 for optical detection of an analyte detected by the lateral flow test strip 128. In some embodiments, not shown, the cartridge 120 may also include an electrochemical assay system in addition to the lateral flow test strip 130, as discussed in detail below. In accordance with some aspects of the invention, the cartridges comprise registration features for mating with a port in the reader device to hold and align the cartridge with certain reader features. The reader features aligned with the cartridge may comprise an electrical connector for reading an electrochemical signal of a cartridge of the type shown in FIG. 1A, and/or an imager for reading an optical signal from a detection zone of a cartridge of the type shown in FIG. 1B, as discussed in detail below.

In further embodiments, the cartridge 120 may also be modified to include a barcode for determining information pertaining to the cartridge, e.g., the identification of an analyte being tested and/or the patient. In accordance with further aspects of the above-mentioned embodiments, the cartridge may also be modified to include a pneumatic pump and/or a test sample separator (not shown), as discussed in detail below. Although some aspects of the invention are disclosed with respect to the cartridges shown in FIGS. 1A and 1B, one of ordinary skill in the art would understand that the concepts discussed herein have many applications and could be implemented in a wide variety of systems and devices, e.g., the i-STAT cartridge as disclosed in Lauks et al., U.S. Pat. No. 5,096,669, the entirety of which is incorporated herein by reference.

Reader Device

In some embodiments, the invention is to a reader device, e.g., a computing device 215 (as discussed with respect to FIG. 2), that is provided for receiving one or more different types of biological sample testing cartridges (as discussed with respect to FIGS. 1A and 1B) through a cartridge receiving port.

FIG. 3A shows an exemplary reader 300 comprising a receiving port 310 in a housing 320. In accordance with some aspects of the invention, the receiving port 310 may be configured to accept multiple cartridge types, including, for example, one or more of: (i) optical test devices comprising qualitative or semi-quantitative lateral flow test systems, (ii) optical test devices comprising qualitative or semi-quantitative microspot array test systems, (iii) electrochemical test devices comprising qualitative or quantitative non-lateral flow and non-microspot array test systems, and (iv) combinations of optical and electrochemical test devices. For example, the multiple cartridge types may include a qualitative lateral flow test device for hCG, a quantitative non-lateral flow test device (e.g., an i-STAT electrochemical cartridge), or a cartridge having both a qualitative lateral flow test and a quantitative non-lateral flow test, e.g., a lateral flow hCG combination with an i-STAT CHEM8 cartridge.

In some embodiments, the lateral flow tests performed include hCG, drugs of abuse, and the like. Exemplary non-lateral flow tests include hCG, K, Na, Cl, Ca, Mg, pH, pO2, pCO2, glucose, urea, creatinine, lactate, CKMB, TnI, TnT, BNP, NTproBNP, proBNP, TSH, D-dimer, PSA, PTH, NGAL, galectin-3, AST, ALT, albumin, phosphate, ALP, and the like. The multiple cartridge types are configured to perform the above-mentioned multitude of test systems using various biological samples including urine, whole blood, plasma and serum, both diluted and undiluted, or with various additives.

In some embodiments, the receiving port 310 may include at least one locating means 330 for properly positioning cartridges in the housing 330 with respect to one or more detectors, e.g., (i) an electrical connector for connecting to a quantitative electrochemical sensor on the cartridge, and/or (ii) an optical imager for imaging an optical assay in the cartridge. In some embodiments, the receiving port 310 may be configured to sequentially receive the multiple cartridge types.

FIG. 3B shows a lip 340 surrounding the receiving port 310. The lip 340 is configured to perform as a light baffle, which substantially blocks external light from entering the housing 320 of the reader 300. In some embodiments, the lip 340 may be made of plastic and/or comprise a sealant such as rubber. In further embodiments, at least a portion of the inside of the reader 300, e.g., an internal coating of the housing 320 around the lip 340, may be formed of a material that blocks light or substantially absorbs rather than reflects light. Preferably, the material is black. In alternative embodiments, the housing 320 may be formed completely opaque by using either black or metal-filled plastic with a colored outer coating or a black or metalized coating on the inside surface of the housing 320. Further, the housing 320 may be formed to inhibit or prevent light entry at edges between separable parts of the housing 320, e.g., an opaque sealant may be used at the edges. In embodiments where the reader 300 also comprises a lighted graphic or character display, the display may be isolated from detection optics to prevent stray light from the display interfering with the detection optics. Preferably, the use of instrument self-diagnostic LEDs or similar elements inside the housing 320 is avoided.

FIG. 3C shows a schematic of the lateral flow device 350, e.g., a cartridge, where a sample 355 is applied with a capillary or pipette 360. In some embodiments, the device 350 may comprise a light baffle 365 for engaging with the lip 340 on the reader 300 to inhibit or prevent external light from entering the receiving port 310. The lateral flow device 350 may also comprise a sample wick 370 for receiving the sample 355, a conjugate pad 372 for labeling a particular analyte with a conjugate, an optional barcode 375, e.g., a two-dimensional barcode, for providing information concerning the type of cartridge and/or the patient, a test window 377 for enabling the reading of the test results, and a waste pad 379 for collecting excess sample and conjugate. In some embodiments, the cartridge may be molded from black or externally metalized plastic, such that stray light cannot be piped through the cartridge body. Furthermore, a sample closure element 380 may be similarly treated to prevent stray light passing along the sample conduit within the cartridge.

FIG. 3D shows the lateral flow device 350 engaged with the reader 300. The reader 300 may comprise one or more detectors for performing the above described one or more test systems. In some embodiments, as shown in FIG. 3D, the reader 300 may comprise an optical imager 390 comprising a sensor array, optical elements, and one or more illumination devices. The optical elements may comprise lens 391 and the sensor array may comprise a camera chip 392, e.g., a charge-coupled device (CCD).

In some exemplary embodiments, the camera chip 392 may, for example, comprise a Canon LiDE210 chip with a 48 bit color resolution specification, where the image is digitized to 16 bits (dynamic range of 0 to 65,536) in each of the red, green and blue channels of a line scan chip. Aptina array sensors, e.g., MT9V034 (6 µm pixel size) or MT9P031 (2.2 µm pixel size), may also be employed. Preferably, the spacial resolution of the CCD is from 4000 to 5000 dpi, e.g., about 4800 dpi, and is able to resolve about from 2 to 10 microns, e.g., about 5.3 microns. Thus, for a line feature size of about 0.5 mm, typical of a lateral flow test strip, the line width is resolved with an image quality of about 90 pixels without magnification.

Figure 4:
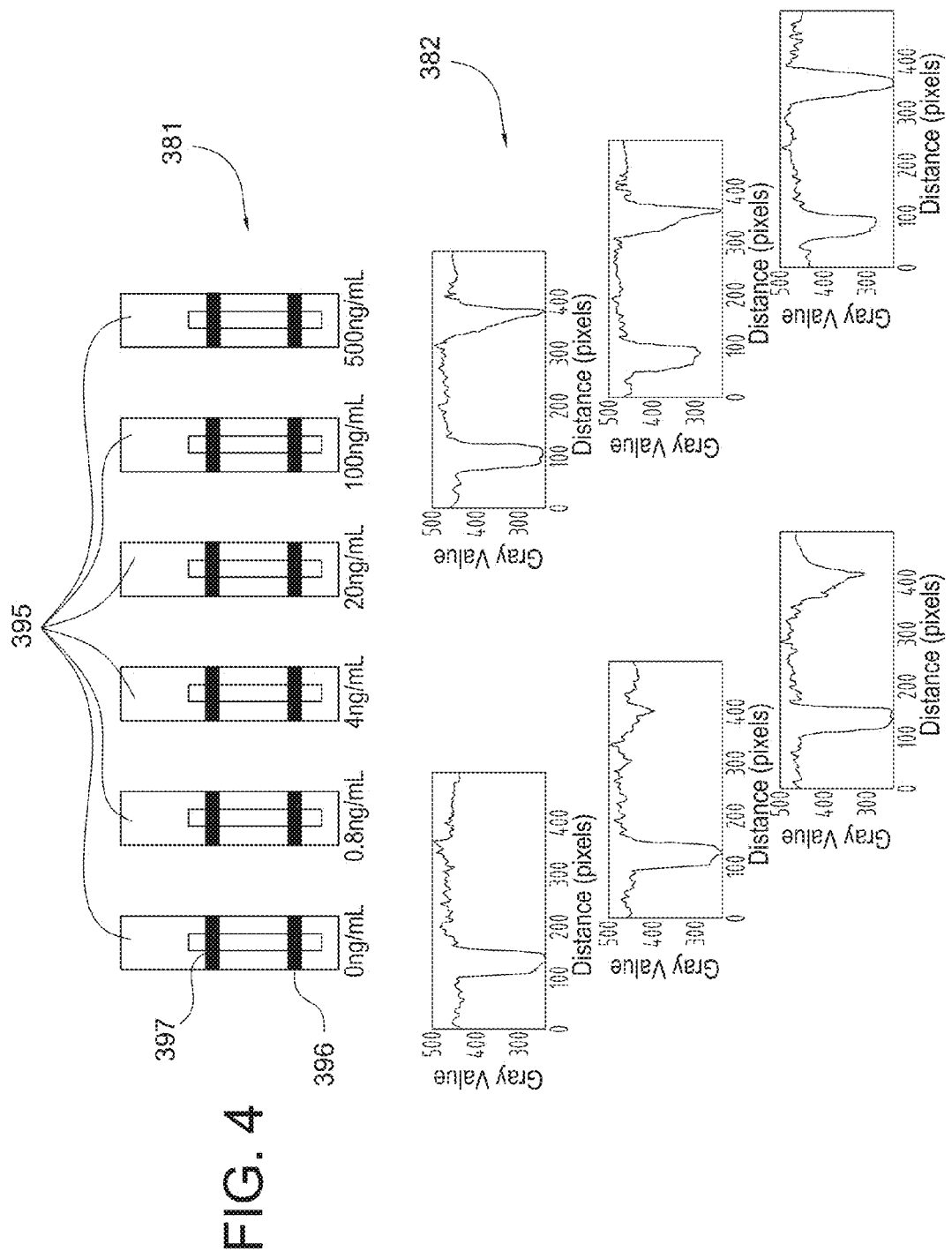
FIG. 4 shows a set of six test strips at a range of concentrations as both a standard electronic image and using an imager chip.
Figure 5:
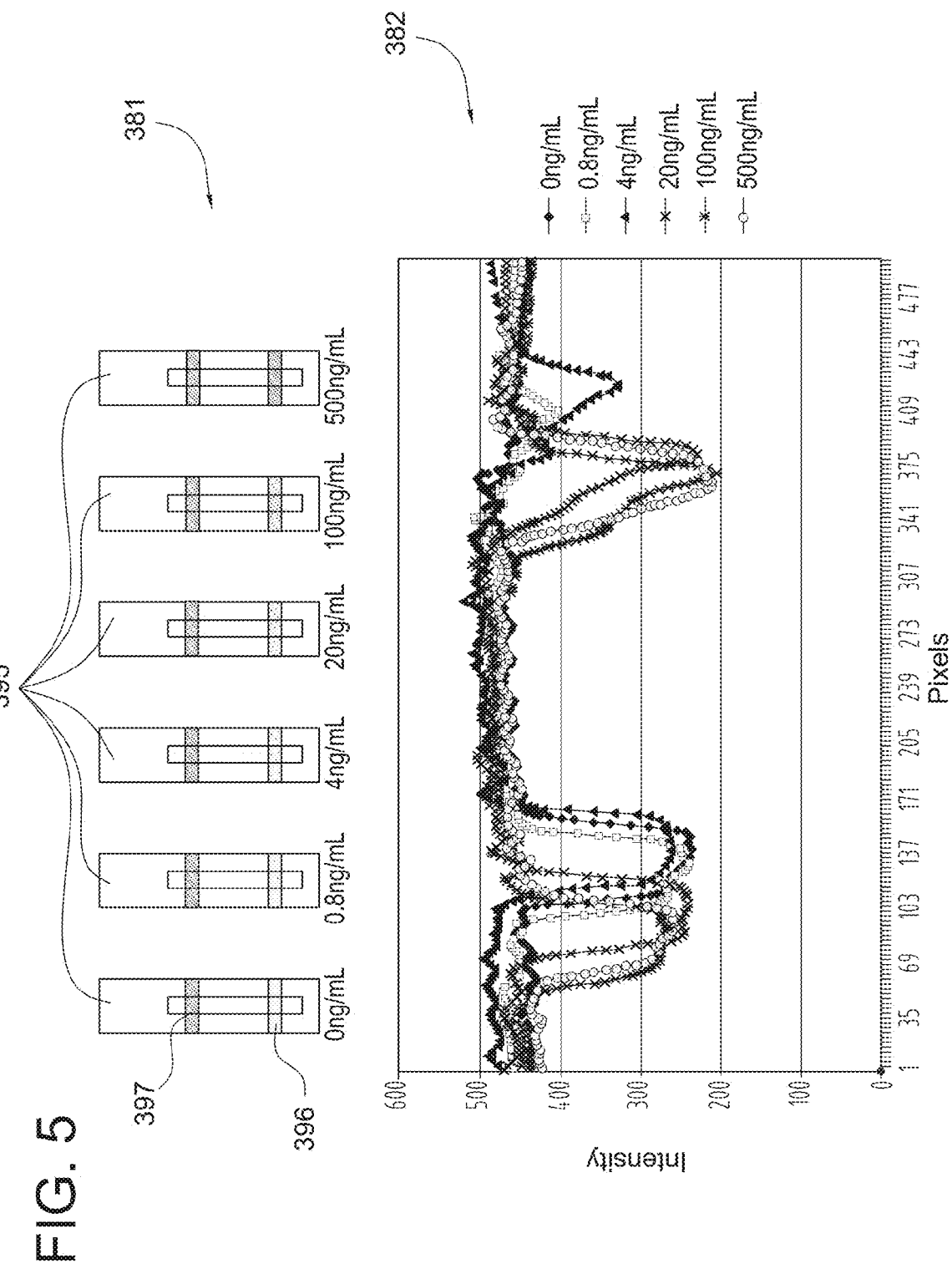
FIG. 5 shows the imager chip traces in a single plot of intensity versus pixel position.

FIGS. 4 and 5 show examples of high resolution color level scale images of several test cartridges treated with known levels of hCG. While the test strips are not necessarily in the focal image plane of the scanner, the test and control lines are imaged sharply enough to be readable quantitatively from 0 to 20 ng/mL hCG. Thus, the imager has a considerable depth of field even though the linear sensor array is close to the object. The illumination and image sharpness across the entire image is also uniform.

Specifically, FIG. 4 shows a set of six β-hCG test strips 395 at a range of concentrations 0-500 ng/mL as both a standard electronic image 381 and using an imager chip 382 within a cartridge housing where control lines 397 and signal lines 396 are located proximate to an imaging area of the imager chip. The data provided in FIG. 4 demonstrates that the imager used for acquiring barcode information can also be used to read the bands of a lateral flow device, i.e., distinguish the position and optical absorbance of the bands. The information is then processed by the reader to determine one or more of: (i) whether the assay was performed properly, (ii) a qualitative result for the presence or absence of an analyte within a sample (e.g., providing a positive or negative test result), (iii) a semi-quantitative result for an analyte concentration with the sample (e.g., wherein the darkness of an optical signal correlates to approximate analyte concentration), or (iv) a quantitative result for an analyte concentration within the sample, as described in further detail herein. The device preferably records and displays the result. FIG. 5 is similar to FIG. 4 but shows the imager traces in a single plot of intensity versus pixel position.

In an alternative embodiment, a CCD line camera (e.g., Mightex TCN-1304-U) may be used as the camera chip 392. The line camera preferably comprises a high-performance B/W board-level line camera, based on a single-line 3648-pixel CCD chip with USB 2.0 (480 Mb/s) interface. This type of CCD line camera has several advantages over area-array counterparts, including high optical linear resolution that allows capture of two-dimensional (2-D) images by moving the object or the CCD perpendicularly to the scan line. See, for example, Fan et al; Integrated barcode chips for rapid, multiplexed analysis of proteins in microliter quantities of blood, in NATURE BIOTECHNOLOGY, 26, 1373-8, 2008, the entirety of which is incorporated herein by reference.

In another alternative embodiment, the camera chip 392 may comprise a linear photodiode or CCD array. In this embodiment, a two-dimensional image of the lateral flow test strip or other planar solid phase multiplex assay test device is acquired by scanning the linear array in a direction perpendicular to its axis. The scanning mechanism preferably has micron or nanometer mechanical resolution and carries the linear array and light sources, which produce a line of light of high uniformity along the length of the linear array, to illuminate the assay test area immediately in front of the array. The line of light is focused to give a high brightness, and high spacial resolution and permit a wide dynamic range of absorbance/reflectance to be detected by the array. Optionally, the line of light may be pulsed or offset a distance ahead of the array so that the imager can exploit time-resolved fluorescence assay labels. For example, a time delay of 200 microseconds can be a achieved by a scanning stage stepping at 100 mm/sec if the line is offset 20 microns (3 to 4 pixel widths) ahead of the linear array. A linear microlens array matching pixels 1:1 and overlying the imaging array can focus on the test area and exclude scattered light from the source and, in addition, can have an integral interference filter to reject the source wavelengths and pass the emission wavelengths.

In prompt fluorescence and reflectance modes the line is preferably projected on the field of view of the microlens-imaging array instead of ahead of the array. Time-resolved detection may also be implemented by pulsing a UV (340-405 nm) light line in the field of view of the linear detector but holding its exposure gate (shutter) off until 200 microseconds after the light pulse is off, followed by integrating for up to 1 millisecond before physically advancing to the next imaging position. In this case, source light falling on the linear CCDs is preferably attenuated by incorporating an optical filter in front of the CCD array. Rejection of 6 ODs in the UV range by a long pass filter may also be desirable.

In another alternative embodiment, the camera chip 392 may comprise time delay and integration (TDI) type linescan array that offers amplification of low light signals and may be used to enhance fluorescence detection sensitivity (e.g., Mightex (Toronto) TCN-1304-U, which in a 1:1 proximity focused design can scan an area over 1 inch (2.54 cm) and is light weight and amenable to inclusion on a portable or handheld instrument). In another alternative embodiment, the camera chip 392 may comprise linear fiber optic arrays that may be used for both light source and imaging elements of the line-scan imager.

As also shown in FIG. 3D, the illumination devices may be comprised of light-emitting diodes (LEDs) 394. For example, multiple wavelength LEDs, e.g., from 405-850 nm, may be used to cover a variety of tests or a single wavelength LED may be used to increase illumination power. Typical wavelengths for measurements (deltas of absorbance) of various analytes are known and depend on the actual assay design, for example 467 and 550 nm for total bilirubin, 600 and 550 nm for albumin, 550 and 850 nm for total protein, and 400 and 460 nm to distinguish conjugated and unconjugated bilirubin. Selection of wavelengths such as these may be achieved by one of ordinary skill in the art.

In alternative embodiments, the illumination may be projected from a laser diode through a cylindrical lens or a fiber optic bundle can be assembled into a linear array. For example, single mode fibers may be used with core diameters of 5 to 10 μm and match reasonably with the pixel size of linear CCD arrays.

An exemplary arrangement of the illumination device and the imager comprises broadband or/and monochromatic illuminators and a color (RBG) optical imager as spectrophotometer. An advantage of this arrangement is the ability to detect multiple wavelengths at once. The arrangement also offers flexibility in the choice of adding new wavelengths of interest. However, this arrangement has a lower sensitivity due to the RGB mask and the simplicity of the spectrophotometry measurement.

Another arrangement comprises a set of discrete LEDs as illuminators and a grayscale optical imager sensitive to all wavelengths of interest. This arrangement is a simpler design implementation and is more sensitive at a given wavelength; however, the choice of wavelengths is fixed. Specifically, the illumination is provided by a set of board-mounted LEDs capable of generating monochromatic excitation in sequence (for multi-color assays) to allow detection of the binding reaction kinetics over time. With respect to the homogeneity of excitation, locating a color reference area or areas on the assay substrate adjacent to the capture zone eliminates or greatly reduces the need for homogeneous excitation. In this embodiment, the reference and detection areas are close enough, e.g., within a few millimeters, such that calibration may not be necessary. However, bright and dark images may be accrued prior to testing in order to assess light non-uniformity and fixed pattern corrections to enhance the signal to noise of the test sequence.

In accordance with some aspects of the invention, the camera chip 392 is used to interrogate the barcode 375 and test window 377 of the lateral flow device 350 sequentially or simultaneously. For example, a cartridge featuring a qualitative β-hCG assay based on immuno-chromatographic instrumented optical detection may be inserted into the reader. Optical detection is achieved by using the internal camera acting both as a two-dimensional barcode reader and as the assay reader. The internal camera may be integrated into an electromechanical measurement module of the reader, which also has a capacity to heat and thermostat the cartridge or portions thereof. Although mainly described in the context of a β-hCG assay, the concepts described above are applicable to other immuno-chromatographic assays.

Figure 6:
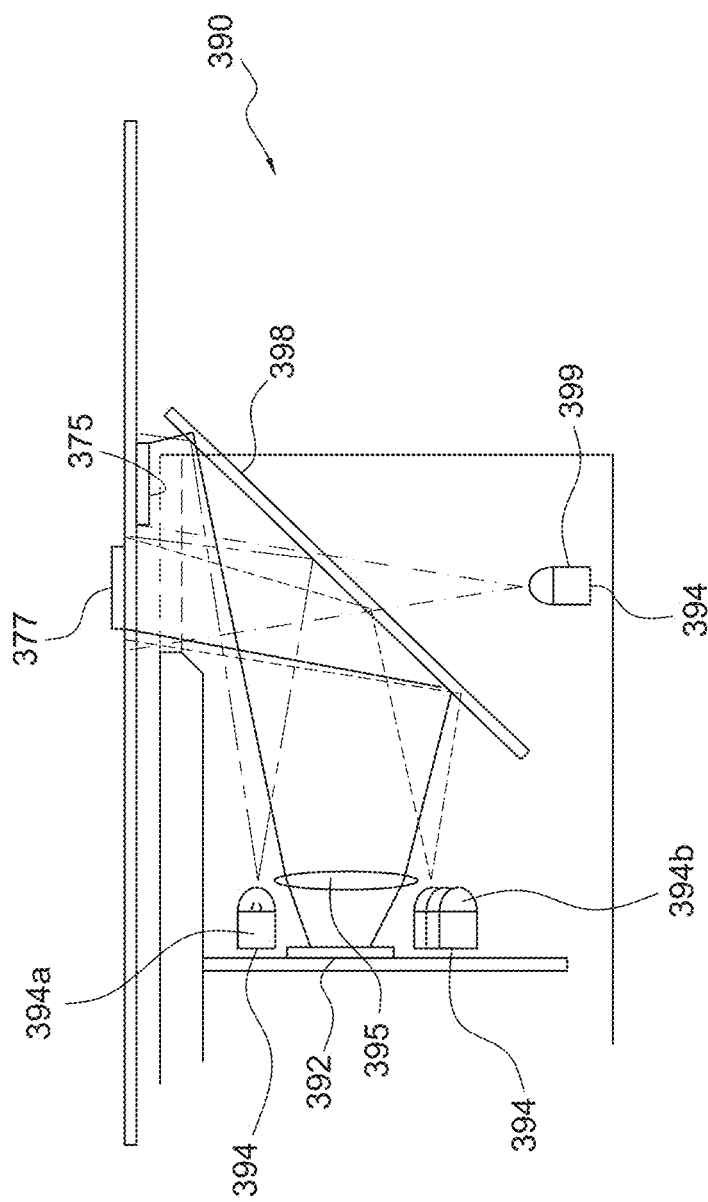
FIG. 6 shows an orientation of optical elements in accordance with some embodiments of the invention.

FIG. 6 shows an example of an arrangement for the optical imager 390. In this embodiment, the LEDs 394 comprise white LEDs 394a for illuminating the barcode 375 on the cartridge and colored LEDs 394b for illuminating the assay area of the strips within the cartridge (e.g., through test window 377). A filter 398, e.g., a short pass filter that reflects 400-900 nm wavelengths, may be positioned between the LEDs and the cartridge such that the filter 398 reflects the light from the white LEDs onto the bar code area and the light from the colored LEDs onto the assay area. An additional LED 399 may also be configured to illuminate the assay area. For example, the additional LED 399 may be a 350 nm LED that illuminates the assay area through the filter 398. The camera chip 392 and the lens 395 may be positioned such that a reflected image of the barcode area and the assay array is capable of being generated at a same time using the filter 398. This arrangement is capable of providing compact optics within a relatively small reader device that also comprises other functional elements that need to interact with the cartridge, e.g., pump actuators, electrical connectors and the like.

Image Processing to Correct for Illumination Non-Uniformity and to Provide a Qualitative, Semi-Quantitative, or Quantitative Analysis In preferred embodiments, several phases characterize lateral flow assay testing and the subsequent processing of information obtained by the imager during and/or after the later flow assay testing. FIG. 7 shows a conceptual representation of the lateral flow assay test strip 130 (as discussed with respect to FIG. 1B) in accordance with the preferred embodiments of the present invention. Upon application of a sample to the test strip 130, the sample flows in the indicated direction by capillary action and comes into contact with an analyte-specific antibody conjugate zone 135 that may be printed in a soluble form. A capture antibody zone 140 located downstream of the analyte-specific antibody conjugate zone 135 may be comprised of analyte-specific antibodies immobilized to the chromatographic medium (e.g., paper, nitrocellulose, etc.). Upon the sample now labeled with conjugate from the antibody conjugate zone 135, reaching the capture antibody zone 140, any analyte present in the sample may be immobilized by virtue of the capture antibodies resulting in localization/concentration of the labeled antigen at the capture antibody zone 140. Material downstream from the capture antibody zone 140 provides a capillary reservoir with which to pull sample through the test strip 130.

The presence of analyte in the sample is detected by the presence of the conjugate label in the capture antibody zone 140. Common labels used in the antibody conjugate zone 135 may include gold colloids (red) and, for example, blue latex particles, etc. However, there is no requirement that the label be detectable in the visible range provided that a suitable detector or imager is employed.

As a function of time, several phases of interest taking place on the test strip 130 can be distinguished. Specifically, the test strip 130 is dry prior to any sample being applied. Wet-up is an initial time period during which the sample flows across the length of the strip. During the wet-up phase, the test strip 130 may experience a visible change as a liquid front moves across the chromatographic medium (e.g., paper, nitrocellulose, etc.). Development is the time when labeling and capture takes place. During the development phase, characteristic bands corresponding to the capture antibody zone 140 and a control zone 145 may become detectable at fixed locations on the test strip 130.

FIGS. 8A-C show examples of images acquired during these various phases (e.g., no sample, wet-up, and development). In FIG. 8A, no sample has been applied. The test strip 130 does not show any visible features (note the absence of characteristic bands). For example, at this stage, the test strip 130 reveals uniform variations associated with illumination and optical data acquisition. Provided the illumination and the optical characteristics of the measurement module do not change during the test phases, these uniformity variations should remain constant. In FIG. 8B, the liquid front has moved across the length of the test strip 130 (e.g., completion of the wet-up phase), and development has just begun (e.g., initiation of the development phase). Capture and control zones, in the form of characteristic bands across the test strip become detectable. In FIG. 8C, development has taken place (e.g., completion of the development phase). For example, the capture and control zones are fully detectable.

Figure 9:
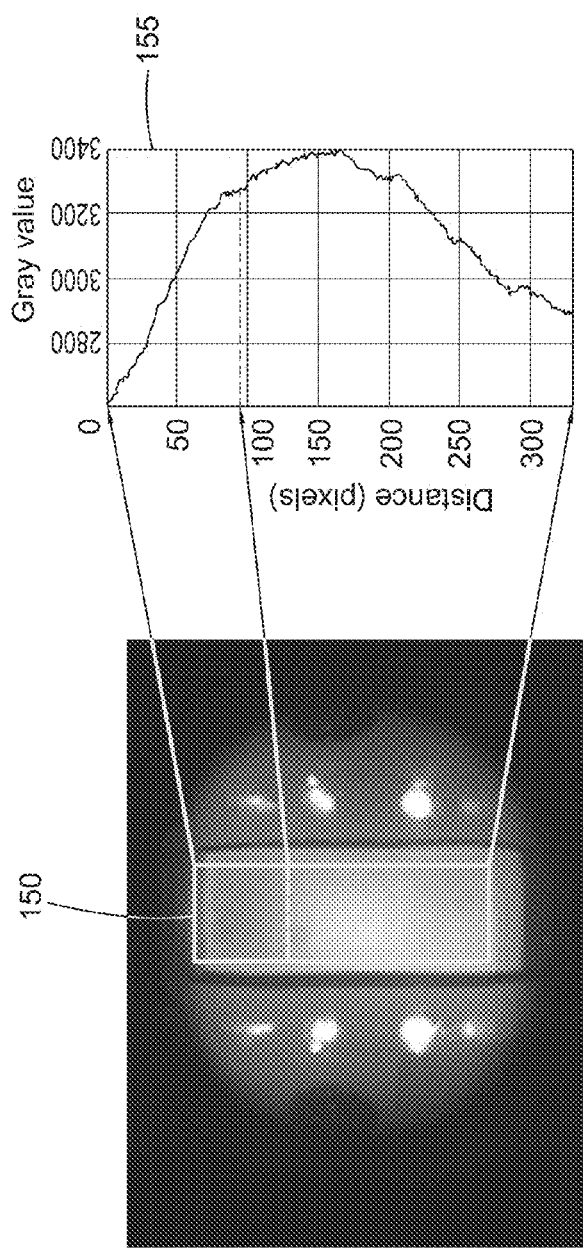
FIG. 9 shows processing of pixel values from image data into graphical plots.

FIG. 9 illustrates an exemplary method performed in accordance with preferred aspects of the present invention for processing a digital image of a lateral flow assay strip to generate a qualitative, semi-quantitative, and/or quantitative digital signal. As depicted in FIG. 9, a rectangular subset 150 of the image is defined to include most of the test strip visible area. The rectangular subset 150 covers most of the test strip area, but may not include the edges of the test strip 130. In lateral flow assays, it may be typical for the fluid flow characteristics on the edge of the test strip to be different from the main area. Not including the edges in the rectangular subset 150 ensures that the flow differences are not corrupting the measurements. Pixel intensity may be integrated across the rectangular subset 150 and plotted on a 2-dimensional chart 155. On the 2-dimensional chart 155, the "x" axis represents the distance along the length of the test strip 130 in the direction of the flow. The "y" axis represents the integrated intensity for a given distance along the test strip 130. The 2-dimensional chart 155 representation of the pixel intensity has benefits for accurately determining the presence or absence of the analyte within the sample (e.g., a qualitative determination), and/or determining a concentration of the analyte within the sample (e.g., a semi-quantitative or quantitative determination), as discussed in further detail below. The integration of the signal is done across the width of the test strip 130 in alignment with the capture antibody zone 140. For each position along the test strip 130, the resulting signal-to-noise ratio of the measurement is improved. For strips where the capture antibody zones 140 are not visible, the plot indicates to the illumination uniformity.

Figure 10C:
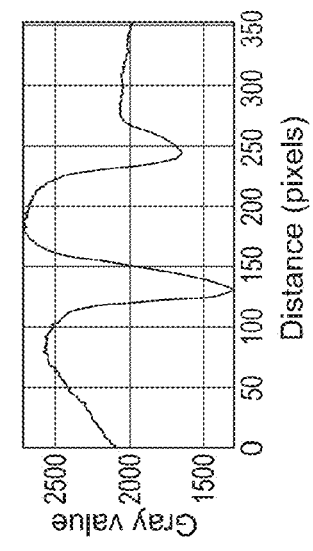
FIGS. 10A-10C show graphical plots of single intensity at various stages of testing.
Figure 10B:
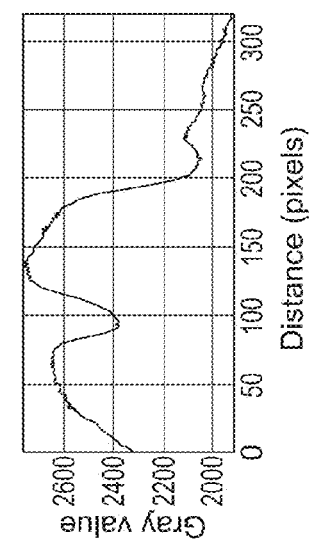
Figure 10A:
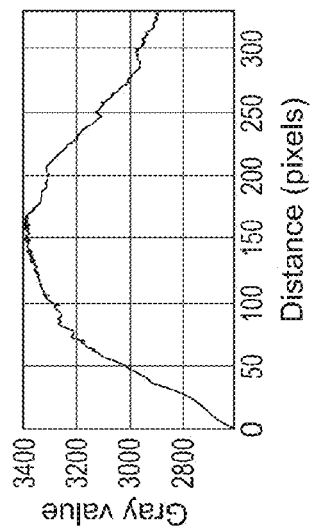

FIGS. 10A-C show examples of graphical plots of the assay signal intensity at the three phases of interest (e.g., no sample, wet-up, and development) for a typical experiment. Specifically, FIG. 10A shows the integrated signal level along the test strip before the sample is applied. The shape of the plot is characteristic of the illumination uniformity along the test strip. FIG. 10B shows the signal level at wet-up. Two dips in the signal are visible at approximately 100 pixels and 220 pixels. Referring to FIG. 8B, the dips correspond to the capture antibody zones 140 (assay and control bands) where development has just begun (e.g., completion of the wet-up phase and initiation of the development phase). FIG. 10C shows the signal level after the development phase. The two dips in signal intensity have become more pronounced. This is consistent with the intensity of the two bands visible in FIG. 8C.

An analysis of the graphical plot depicted in FIG. 10C reveals that a quantitative measurement of the relative intensity of the dips may be difficult. Without being bound by theory, a main contributing factor to this difficulty may be the lack of uniform illumination. Accordingly, one of the possible methods to eliminate, or at least reduce, the effect of non-uniform illumination is to subtract a reference image from the image taken after the development phase. FIGS. 11A-C depict images and graphs that illustrate results from the subtraction of the image (shown in FIG. 11B) taken after the development phase from the image taken at the wet-up phase (shown in FIG. 11A). The corresponding 2-dimensional graphical plot (shown in FIG. 11C) shows that the effect of lack of background uniformity has been virtually eliminated. Note that a bias may be introduced to normalize the difference image and ensure that all the intensity values are positive. Although subtraction and bias adjustment may be performed manually, these steps may be automated via software implementation in accordance with some aspects of the present invention. The graphical plot in FIG. 11C features two peaks that correspond to the capture bands. Unlike the plot in FIG. 10C, a ratio measurement can easily be made on the processed plot of FIG. 11C to achieve a qualitative, semi-quantitative, and/or quantitative determination, as discussed in further detail below.

In alternative or additional embodiments, various choices for a reference image to facilitate the qualitative, semi-quantitative, and/or quantitative measurement of the relative amplitude of the signals may be utilized. For example, with respect to FIGS. 11A-11C, a reference subtraction method based on subtraction of the image taken after the development phase from the image taken at wet-up phase was described. The use of the image taken after the wet-up phase as a reference image produced adequate results for the material and optical characteristics of the particular lateral flow assay strip. However, for lateral flow assay strips with different characteristics, it may be advantageous to use a different reference image. For example, a subtraction of the image taken before the sample is applied from the image taken after the development phase may be performed. FIGS. 12A-C depict images that pertain to the subtraction of the image taken after the development phase from the image taken before the sample is applied. For this particular case, the corresponding 2-dimensional graphical plot in FIG. 12C shows that the effect of lack of background uniformity has not been completely eliminated. However, the graphical plot in FIG. 12C features two clearly distinguishable peaks that correspond to the capture bands and a ratio measurement can easily be made to achieve a qualitative, semi-quantitative, and/or quantitative determination, as discussed in further detail below.

Figure 13:
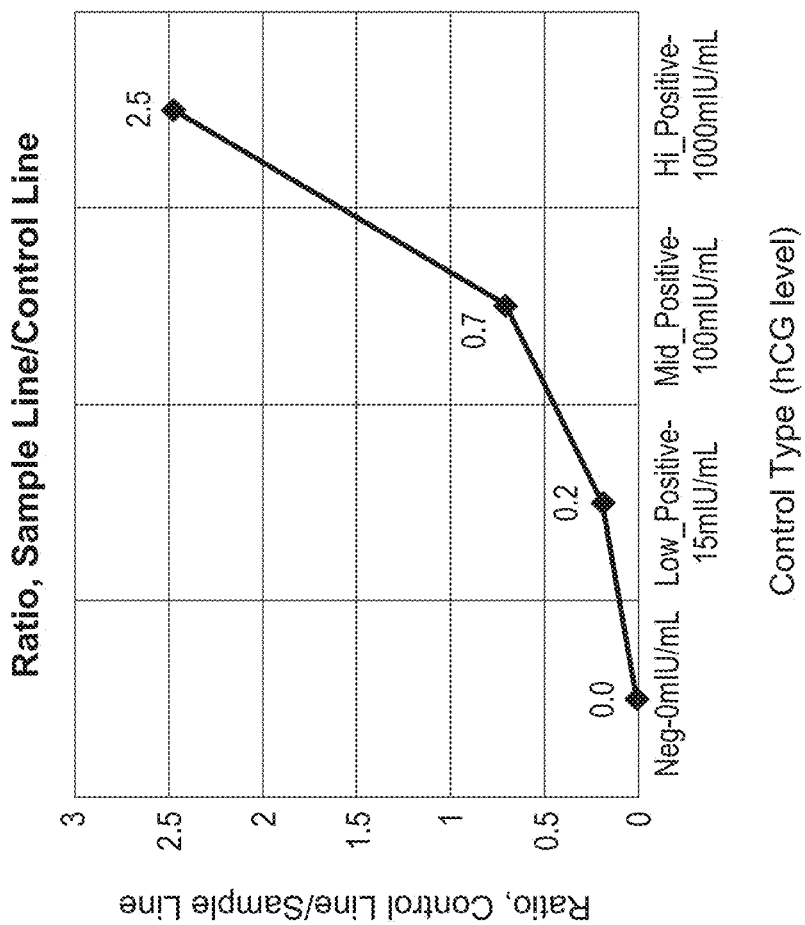
FIG. 13 shows a plot of ratios of measured peaks in accordance with preferred embodiments of the invention.

In preferred embodiments, the presence or absence and/or the concentration of the analyte present in the sample may be determined and/or quantitated using the graphical plots of signal intensity, as described above. Specifically, one way to quantify the lateral flow assay response is to measure the relative size of the peaks corresponding to the capture antibody and control zones. A ratio of the peak amplitudes can be made for various concentrations of analyte and further processed into response curves. FIG. 13 depicts a plot of the ratios between the sample and the control lines for the known analyte concentration values between 0 and 1000 mIU/mL, as described with respect to FIGS. 12A-C. The ratio plot shows that the optical measurement set up and the signal processing method described herein is capable of measuring the concentration of the analyte for the known concentrations. Furthermore, the processing method is capable of measuring a response for concentrations below the stated detection threshold of the lateral flow assay strips.

Lateral Flow Device

Figure 14:
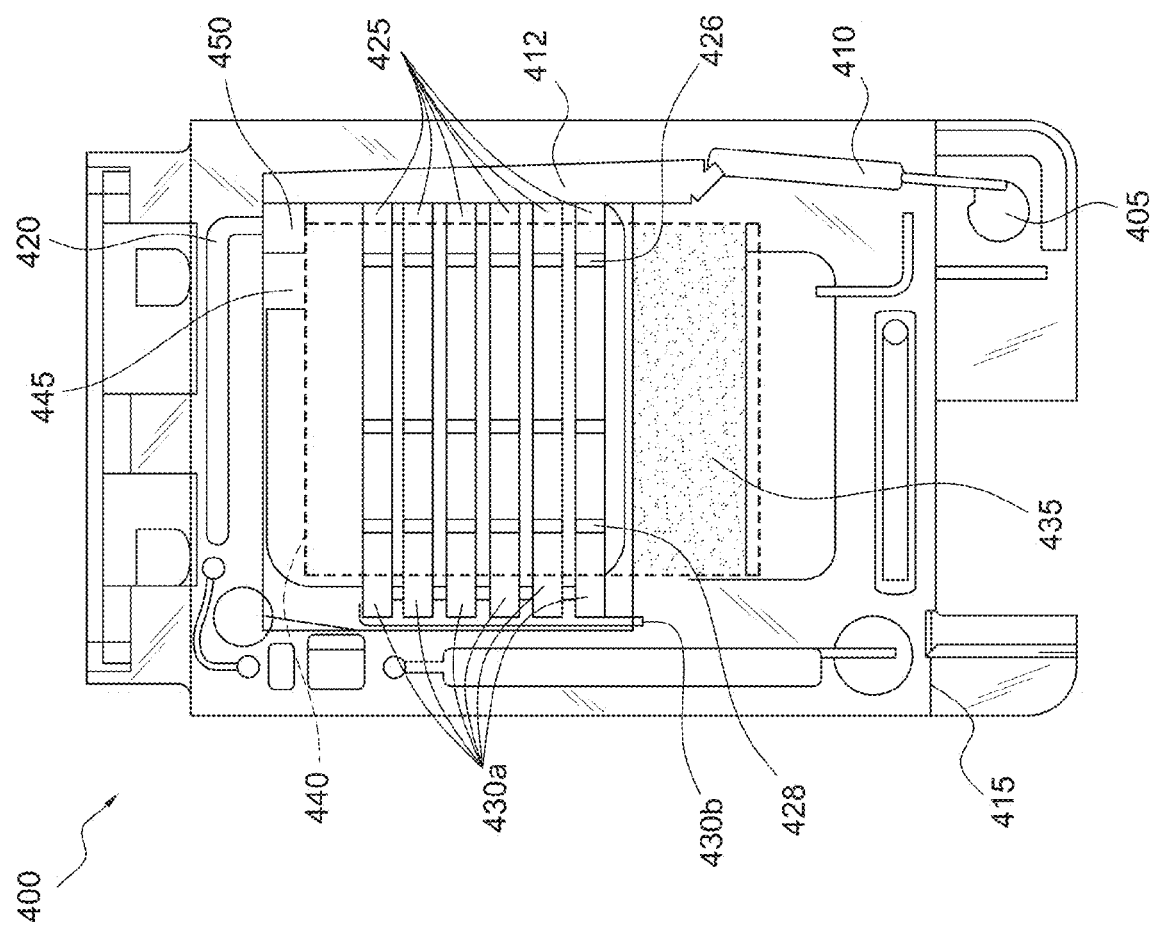
FIG. 14 shows a lateral flow test device adapted to mate with an instrument port.

FIG. 14 shows a lateral flow test device 400 in accordance with one aspect of the invention. In this embodiment, the basic features of a commercial i-STAT cartridge are retained (See, e.g., U.S. Patent Publication No. 2011/0150705, which discloses a non-lateral flow i-STAT cartridge) while integrating lateral flow features into the device 400. As shown, the test device 400 comprises lateral flow test systems without an electrochemical test system, although in other embodiments the test device 400 may incorporate the use of both test systems in the same device.

As shown, the device 400 comprises an entry port 405 configured to receive a sample. A sample holding chamber 410 is provided in fluid communication with the entry port 405 and is configured to act as a conduit for receiving the sample, optionally via capillary action. A capillary sample distribution port 412 is provided as an extension of the sample holding chamber 410 and is optionally formed into a slot in the base of the device and may be closed by an optical front cover 415. The optical covering 415 is formed of a transparent material, e.g., a UV transparent material, and forms the cover of the device 400. The capillary sample distribution port 412 also optionally connects to an inlet side of sample channel 420, which may be included, for example, to deliver sample to one or more electrochemical sensors (not shown) on the device. The capillary sample distribution port 412 is also in fluid communication with a plurality of lateral flow test strips 425 positioned within a capillary distribution channel. The device 400 may, for example, comprise "n" number of lateral flow assay strips 425 comprising "x" number of assays.

The strips 425 are configured to allow the sample to flow by capillary action away from an application site on the test strip. In exemplary embodiments, as the sample progresses further away from the application site in each respective strip, the sample preferably comes into contact with a conjugate pad 426 comprising a conjugate label, e.g., an analyte-specific antibody that is printed in soluble form onto the wick downstream of the application site. The conjugate label may bind to the analyte contained within the sample (if present), and forms a sample and conjugate complex. As the sample and conjugate complex progress further along the wick, the complex preferably comes into contact with a capture zone 428, e.g., a chromatographic medium (paper, nitrocellulose etc.) zone located downstream of the conjugate pad. The capture zone may be comprised of analyte-specific antibodies that are immobilized to the wick. Upon reaching the capture zone, any analyte present in the sample and conjugate complex, will be immobilized by virtue of the capture antibodies resulting in localization/concentration of the labeled antigen at the capture zone. The presence of the analyte is detected by the presence of the conjugate label in the capture zone. The labels may include, for example, gold colloids or colored latex particles. However, there is no requirement that the label be detectable in the visible range provided that a suitable detector/imager is provided, e.g., a fluorescent or phosphorescent label activated by a light source also integrated into the reader housing may be used. The strips may also comprise control zones, which indicate passage of the fluid to the capture zone 428 ensuring a proper test has been achieved. With a successful test, the control zone should indicate a positive result regardless of whether the sample contains the analyte of interest.

Additional wick material located downstream from the capture zone provides a waste pad 430a, which is configured to pull the sample across the wick within the cartridge. In some embodiments, a reservoir 430b is formed as a slot at a terminal end of the strips 425 and is closed by the optical cover 415. The reservoir 430b is configured to draw the sample through the strips 425 from the capillary sample distribution port 412.

As discussed above, the device 400 may also comprise a barcode 435, e.g., a 2D-barcode. The barcode 435 is preferably positioned on the device 400 such that a camera chip in the reader device is capable of imaging the assays on the strips 425 and the barcode 435 sequentially or simultaneously. For example, the strips 425 and barcode 435 may be positioned within an imaging area 440 that covers both the strips 425 and the barcode 435. The transparency of the optical cover 415 enables the imaging area 440 to be illuminated by an illumination device, e.g., a fiberoptic ring epi-illuminator, and for an image to be taken of the assays on the strips 425 and the barcode 435.

FIG. 14 also shows that the device 400 may comprise at least one mirror that forms a 2 pass optical cuvette 445 for detection of total protein (UV spectrum), bilirubin, and hemoglobin (visible spectrum) by use of a microscale-fiberoptic-coupled UV-VIS diode array spectrometer. A short porous filter 450 passes the sample, e.g., plasma, into the optical cuvette 445 from the capillary sample distribution channel. As is shown, conduit 412 may be bifurcated, optionally adjacent optional filter 450, thereby segmenting a blood sample into an optical assay channel and an electrochemical assay channel.

In preferred embodiments, a detector may be used to determine the presence or absence of a positive result in the lateral flow assay. The detector may be an imager or barcode reader element, e.g., a diode or laser scanners that function by reflectance, a CCD or CMOS reader or similar camera devices, as discussed above in detail. For example, the imager may be integrated into a reader that mates with the lateral flow device. When the lateral flow device is inserted into the reader, an illumination source and the imager are activated. As discussed above, the illumination sources can be monochromatic or cover a broad spectrum within or outside of the visible range. For example, monochromatic sources used in combination with a color separating barcode sensor enable fluorescence assay detection.

This embodiment also enables the determination of multiple analytes, e.g., drugs of abuse, assayed simultaneously, with each drug having a distinct capture zone. For example, the pattern of "bars" or "dots" detected by the reader establishes which analytes are present and which are absent. In addition, an imaging area of the device can be divided into two distinct zones fulfilling different functions. For example, the imaging area can formed to be about 12×6 mm. One part of the imaging area may be used to print the barcode information that could be used for identification of the cartridge type and any additional parameters necessary to evaluate the result. Another part of the imaging area may be used to print the arrayed capture zones. In addition, "comparator" zones comprising positive and negative controls may also be printed on the device in the imaging area. In order to detect contrast between positive and negative controls, or the presence or absence of conjugate labels by the barcode reader, an automatic gain control feature may be utilized to optimize a dynamic range of the acquired image to maximize a number of levels. A threshold value determination may be used to characterize each capture site as "positive" or "negative."

The lateral flow device may be assembled comprising several "wicking" elements including a sample deposition element that filters, for example, blood cells from the sample so that the assay proceeds with plasma. The conjugate zone may also be applied as a separate element previously impregnated with conjugate or other sample treatment reagents. Furthermore, the device may be assembled as a single optical assay cartridge or integrated with electrochemically based assays in the same cartridge, as discussed in further detail below.

Figure 15B:
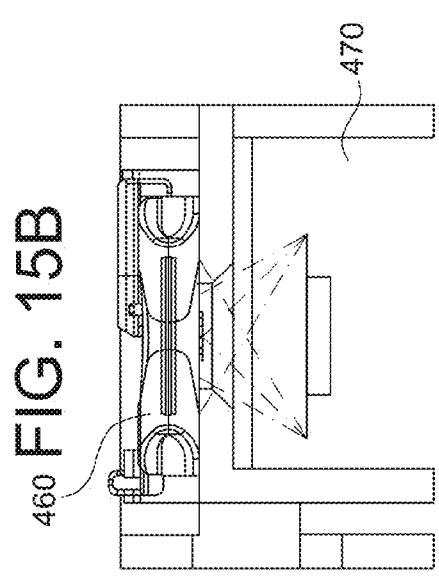
FIGS. 15A-15C show side, plan and front views, respectively, of a lateral flow test device adapted to mate with an instrument port.
Figure 15A:
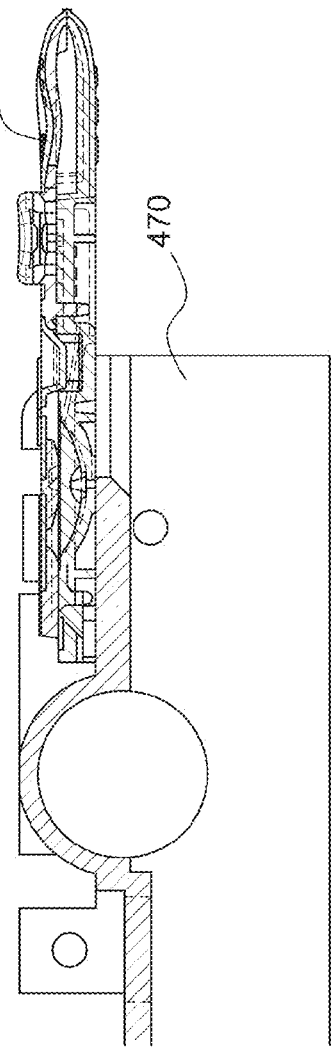
Figure 15C:
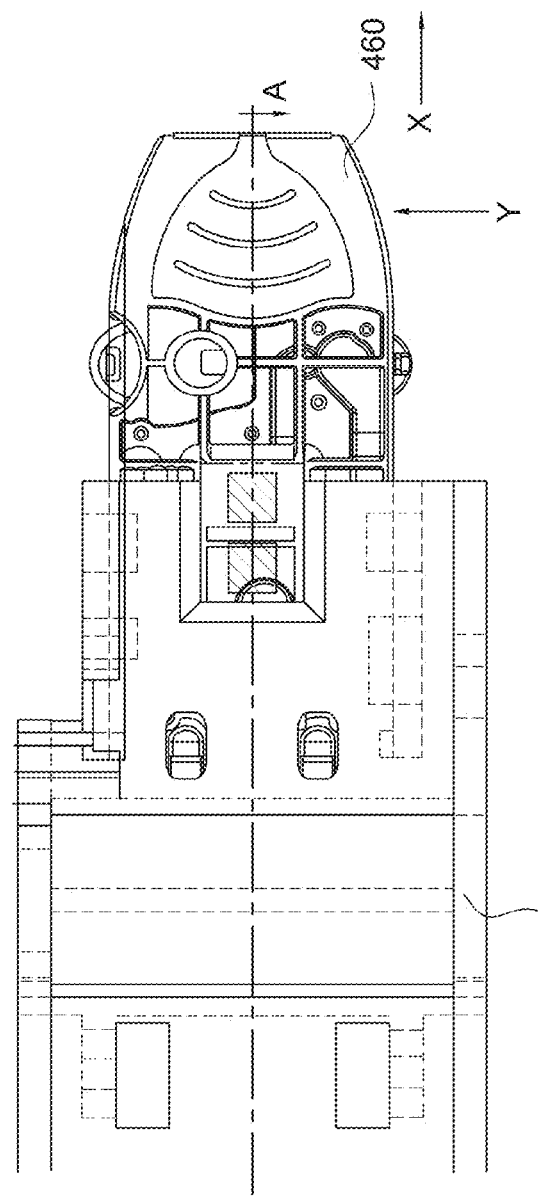
Figure 16C:
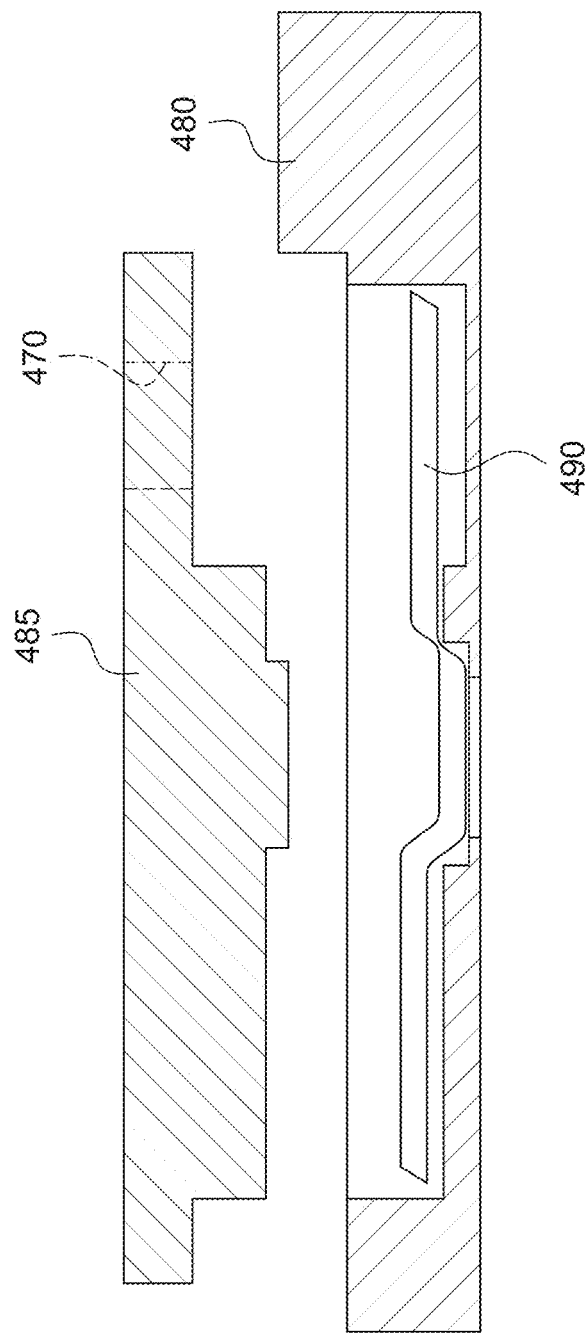

FIGS. 15A-15C show side, plan, and front views, respectively, of a folded lateral flow cartridge 460 for a single lateral flow strip. The cartridge 460 is shown engaged with reader 470. FIGS. 16A-16C show perspective and side views of a bottom portion 480 and a top portion 485 of a lateral flow cartridge in accordance with another embodiment of the invention. In some embodiments, the top portion 485 is configured to receive application of a sample through a sample entry port 470 of the cartridge. The sample entry port 470 is in fluid communication with an application site on the sample wick or strip 490, as described above with respect to FIG. 14.

Microspot Array Device

As an alternative to reading a lateral flow device, the imager within the reader may be configured to read a microspot array within a cartridge. In this embodiment, individual reagents are immobilized as spots in an array on a substantially planar surface within the cartridge, as discussed above. Each spot in the array is assigned a specific coordinate (row x; line y) and has preselected dimensions, e.g., circular with radii in the range 10-1000 µm. This information may be either pre-programmed into the reader or can be decoded from a corresponding barcode, which may be read before, after or simultaneously with the reading of the microspot array. Consequently, the image capture software can identify each spot and determine from the spot intensity, for example, one or more of the presence or absence of the analyte, analyte concentration, or a calibration signal. Adjacent areas of the test device that are accessible to the imager can also provide a flat field correction grid which acts as an integrated internal assay set of reference spots.

Figure 17A:
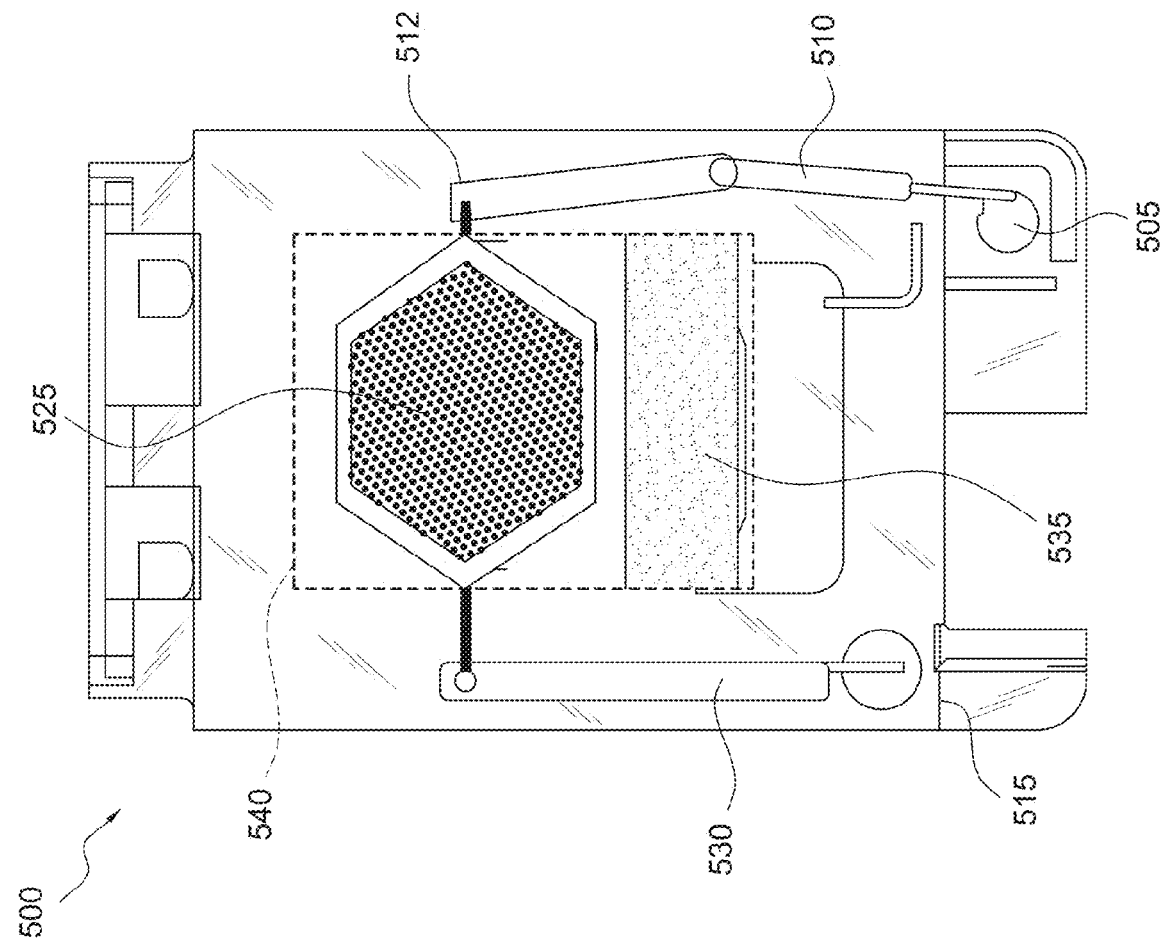
FIGS. 17A and 17B show microarray test devices adapted to mate with an instrument port.
Figure 17B:
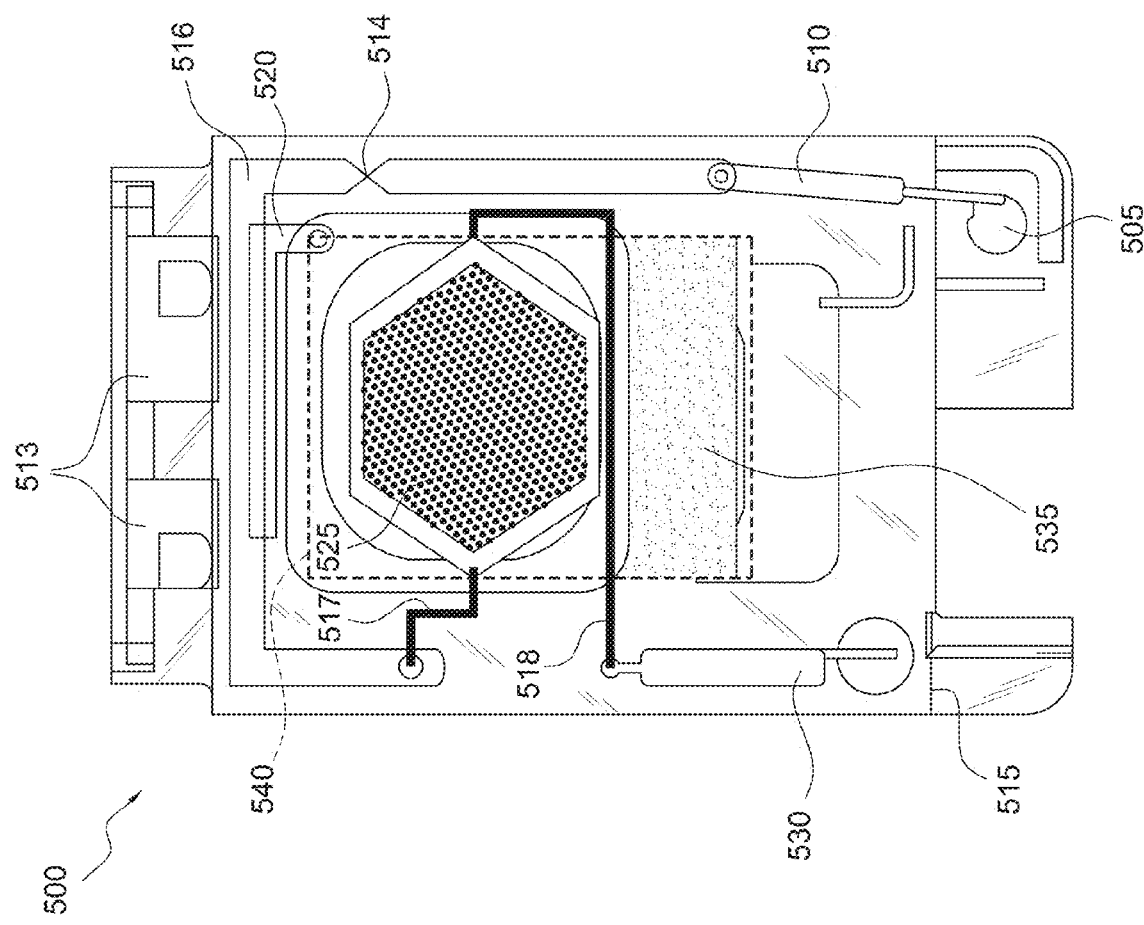

FIGS. 17A and 17B show test devices 500 (cartridges) having microspot arrays in accordance with some embodiments of the invention. FIG. 17A shows a cartridge having a microspot array without electrochemical features. FIG. 17B shows that the basic electrochemical features of a commercial i-STAT cartridge may be retained (See, e.g., U.S. Pat. Nos. 5,096,669; 5,447,440; 6,750,053; 7,419,821; and 7,682,833, and U.S. Publication No. 2011/0150705, the entireties of which are incorporated herein by reference and which disclose non-lateral flow i-STAT cartridges) while integrating microspot array features into the device 500. The individual reagents may be printed and immobilized as spots using known methods. See, e.g., Cozzette et al., U.S. Pat. No. 5,200,051, the entirety of which is incorporated herein by reference. Thus, the test device 500 may comprise microspot array test systems without electrochemical test systems (FIG. 17A) or the test device 500 may incorporate the use of both test systems on the same device (FIG. 17B).

As shown in FIG. 17A, the device 500 comprises an entry port 505 configured to receive a sample. A sample holding chamber 510 is provided in fluid communication with the entry port 505 and is configured to act as a conduit for the sample. A capillary sample distribution port 512 is provided as an extension of the sample holding chamber 510 and is formed into a slot in the base closed by an optical cover 515. The optical covering 515 is formed of a transparent material, e.g., a UV transparent material, and forms the front cover of the device 500. The capillary sample distribution port 512 is in fluid communication with a microspot array 525 positioned within a microspot array chamber. The microspot array 525 (e.g., comprising capture antibodies or antigens) comprises a plurality of spots for multiplex assays. For example, the microspot array 525 may have an approximate capacity for about 600 spots, which would permit high level protein and DNA multiplex assays. After the sample has passed through the microspot array, e.g., through wicking, the sample may be delivered through a waste conduit to waste chamber 530.

In some embodiments, the device 500 may also comprise a barcode 535, e.g., a 2D-barcode. The barcode 535 is positioned on the device 500 such that a camera chip in the reader is capable of imaging of the microspot array 525 and the barcode 535 at a same time. For example, microspot array 525 and barcode 535 may be positioned within an imaging area 540 that covers both the microspot array 525 and the barcode 535. The transparency of the optical cover 515 enables the imaging area 540 to be illuminated by an illumination device, e.g., a fiberoptic ring epi-illuminator, and for an image to be taken of the microspot array 525 and the barcode 535.

In embodiments in which the microarray test system and the electrochemical test system are comprised on the same test device, the microspot array chamber may be configured in series or in parallel with an electrochemical sensor channel. The test device 500 of FIG. 17B, for example, is substantially as described above in connection with FIG. 17A, but also includes the same type of fluidic designs and capabilities rendering its suitable also for electrochemical assays, and shows electrochemical and optical sensing systems operating in series. The device 500 comprises an entry port 505 configured to receive a sample. A sample holding chamber 510 is provided in fluid communication with the entry port 505 and is configured to act as a conduit for the sample. After optionally being pushed through a capillary stop 514 the sample is delivered to an electrochemical sensing conduit 516 in which an immunoassay is formed on one or more electrodes 513. After electrochemical sensing, the resulting fluid is directed through conduit 517 to microspot array 525 positioned within a microspot array chamber such the sample is directed to the microspot array. The microspot array 525 (e.g., comprising capture antibodies or antigens) may have a plurality of spots for multiplex assays. Thus, in this embodiment, the sample may be first processed in the electrochemical section and then pushed into the optical section. In this embodiment, the solution may comprise both electrochemical and optical substrates for imaging. As the electrochemical detection is completed, the substrate is delivered to the microspot array chamber subsequent to the electrochemical detection. The sample remains in the microspot array chamber during image interrogation in chemiluminescence and precipitating fluorescence substrate based assays. After the sample has passed through the microspot array, the sample may be delivered through a waste conduit 518 to waste chamber 530.

Figure 25:
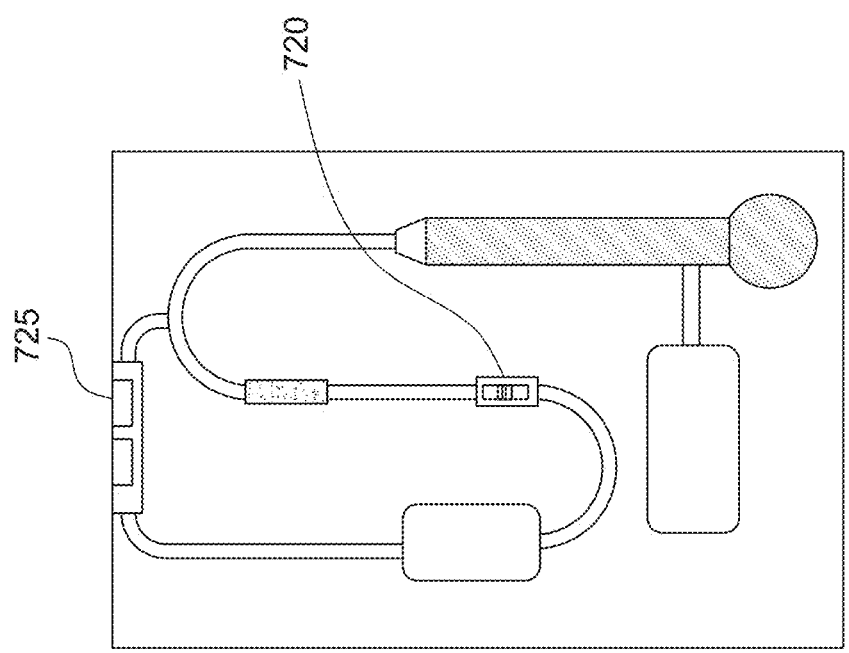
FIG. 25 shows another embodiment of a test device with pneumatic mixing of a labeled antibody with a sample further comprising lateral flow capture zones in one channel and electrochemical detectors in another channel.

In another embodiment, sample fluid from the holding chamber 510 is divided into two streams. One stream is directed to the electrochemical sensor via conduit 520 and another stream is directed to the microspot array in a manner similar to FIG. 17A. The resulting streams undergo separate analysis by electrochemical and optical processes, as described above, and may be separately directed to waste chamber, or may be combined and directed to the waste chamber together. FIG. 25, discussed below, shows a similar embodiment allowing parallel optical and electrochemical detection.

Figure 18:
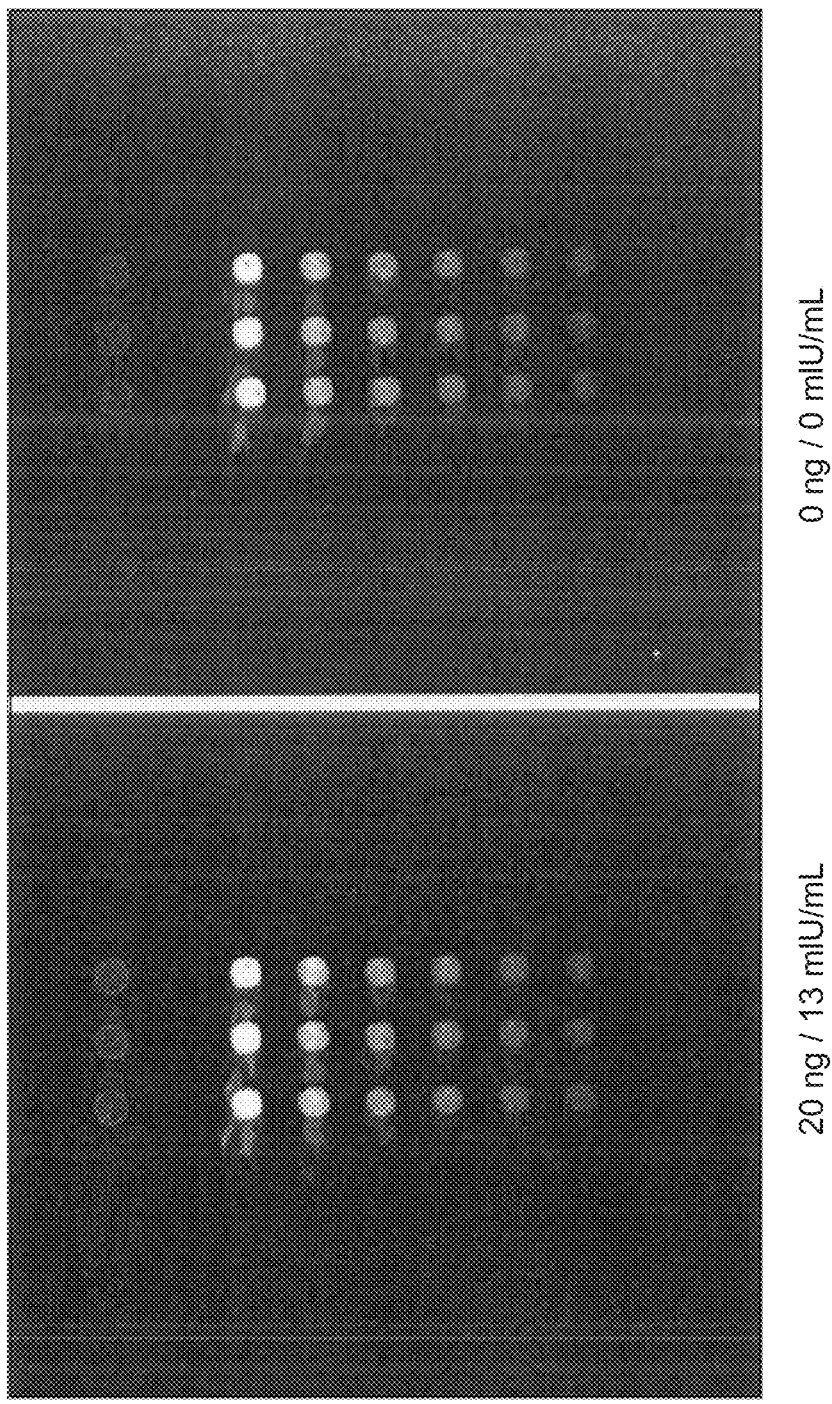
FIG. 18 shows a fluorescent image of a test device with a microspot array.

FIG. 18 shows a fluorescent image of a test device with a microspot array. In one aspect, the monochromatic image illustrated in FIG. 18 is what is viewed by the imager. The calibration standards contained within the array may also be used as grid landmarks for auto-alignment of the imager. In some embodiments, ultra-bright conjugate labels may be used for low cost or low sensitivity imagers.

For calibration, it is possible to print a dilution series comprising, for example, IgA, IgG, IgM, IgD, IgE within the microarray that contains antigens or antibodies for the array of test analytes. The printed reagents can generate standard curves for each within the sample. Aspects of the calibration may include homogeneity of the illumination intensity. The calibration spots may be collocated next to the assay spots to minimize variability. In an alternative embodiment, an image may be captured prior to the test cycle for calibration purposes. Advantageously, any factors that influence the array test spots will also affect the calibration spots. Therefore, common influences such as rheumatoid factor, lipemia, hemolysis, intravenous fluids, immunoglobulins and the like, which can change the slope of the calibration curves are corrected, thus providing a quantitative measurement for each of the tests. Another advantage of this assay is the inclusion of replicates (e.g., three as shown for each calibrator and test in FIG. 18).

In some embodiments, off axis illumination arrangements as discussed above with respect to FIG. 6 may reduce or eliminate specular reflections allowing various substrates with different reflectivity properties to be used in the device. For example, the support substrates may include paper, micro/nano-porous filters, glass, plastic, silicon, alumina, polymer gels, and the like. These substrates may be incorporated into various kinds of microfluidic structures of the device, e.g., the structures shown in FIG. 17B.

Another advantage of the microspot array is the ability to multiplex. For example, different classes of patient responses may be determined by a color of the emitted light. One of ordinary skill in the art would understand that many analyte targets may be chosen, e.g., classes of drugs, different classes of cytokines and inflammatory markers.

The present embodiment may also comprise nanoparticle phosphor (time-resolved fluorescent) immunoassays, e.g., using Seradyn Eu-chelate-loaded time-resolved assays. Two light sources may be used, e.g., a pulsed blue LED and a xenon lamp. Fluorescein, ruthenium chelate and platinum-porphyrin can be excited in the blue and UV range, whereas europium chelate is excited only in the UV. While fluorescein is prompt and disappears in a few nanoseconds, Ru emission disappears after 50 μsec, Pt after 250 μsec, and Eu chelate reaches its peak emission at 250 μsec and lasts several milliseconds. One of ordinary skill in the art would understand that this is just one example of a three-level fluorescence multiplex labeling format without the need for multiple optical filters, and the disclosed invention is not limited by this arrangement.

Figure 19:
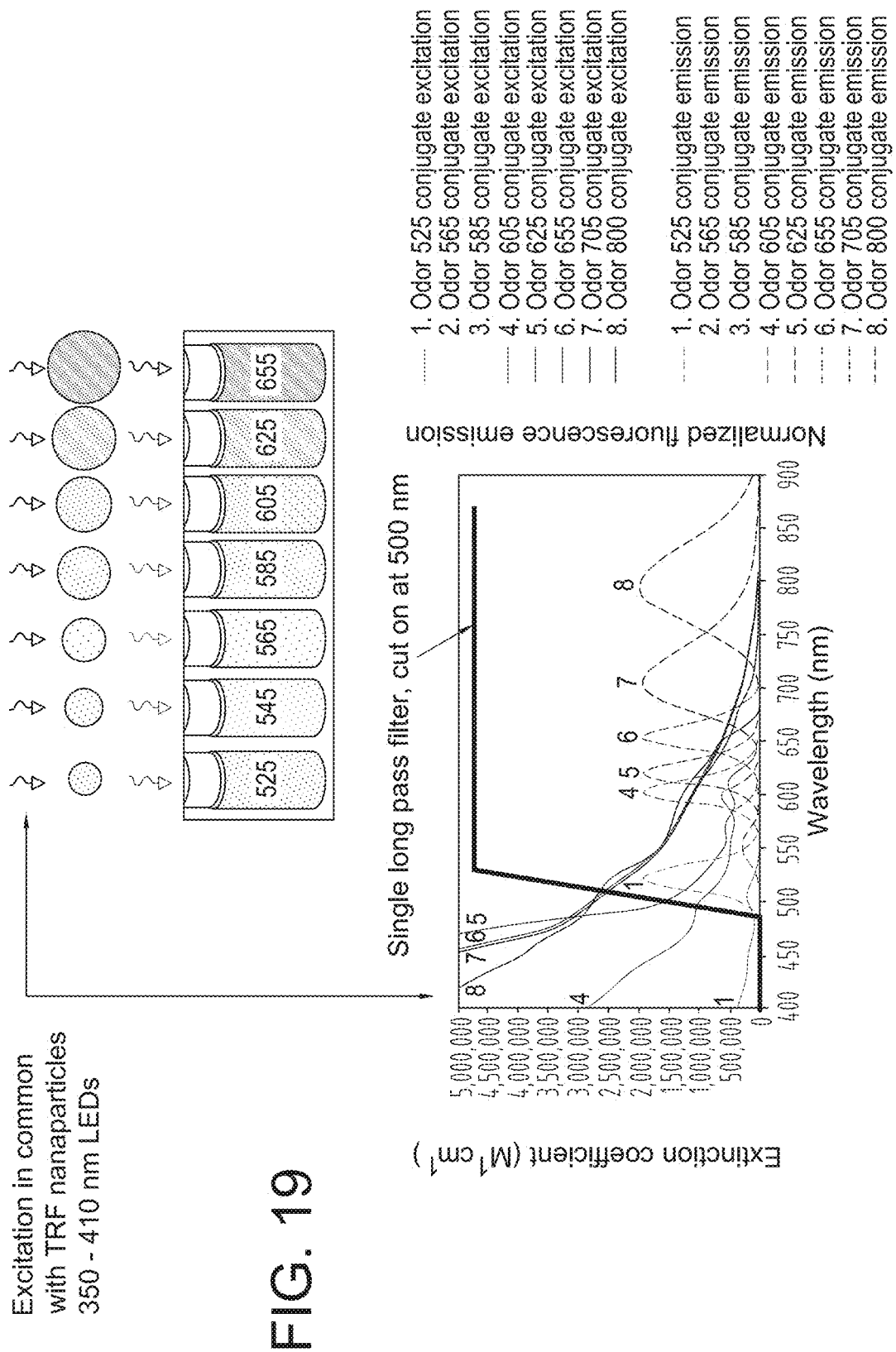
FIG. 19 shows quantum dot features that may be used alternatively in the array of FIG. 18.

FIG. 19 shows a fluorescent image of an exemplary test device with a quantum dot array.

Cartridge with Lateral Flow Fluidics and Conductimetric Fluid Position Detection In some embodiments, the cartridges or devices may further comprise detection components for conductance-based determination of the position of a fluid within a microfluidic circuit of the cartridge and lateral flow fluidic components for the active movement of the fluid through the cartridge based on the determination of the position of the fluid. For example, gold electrodes on a flexible or rigid printed circuit may be located within the channels of the microfluidic circuit at points important to the functional control of the fluidic device. A change in conductance/impedance between pairs of electrodes occurs when the fluid is in contact with the pair and forms a contiguous fluid bridge between them. Thus a measured signal consistent with a fluid partially or entirely between the pair of electrodes means that its position is known by the analytical system (e.g., the reader and/or the cartridge).

The analytical system may comprise a pump whose pressure or displacement is under logic or computer control (e.g., computing device 215, discussed below). The pump may be connected to the microfluidic circuit and may be used to automatically move the fluid until a conductance/impedance change indicates the fluid is bridging a chosen pair of electrodes, and thus occupies a known position. In embodiments, the pump may be a pneumatic pump, a hydraulic pump, a syringe, or the like.

Figure 20:
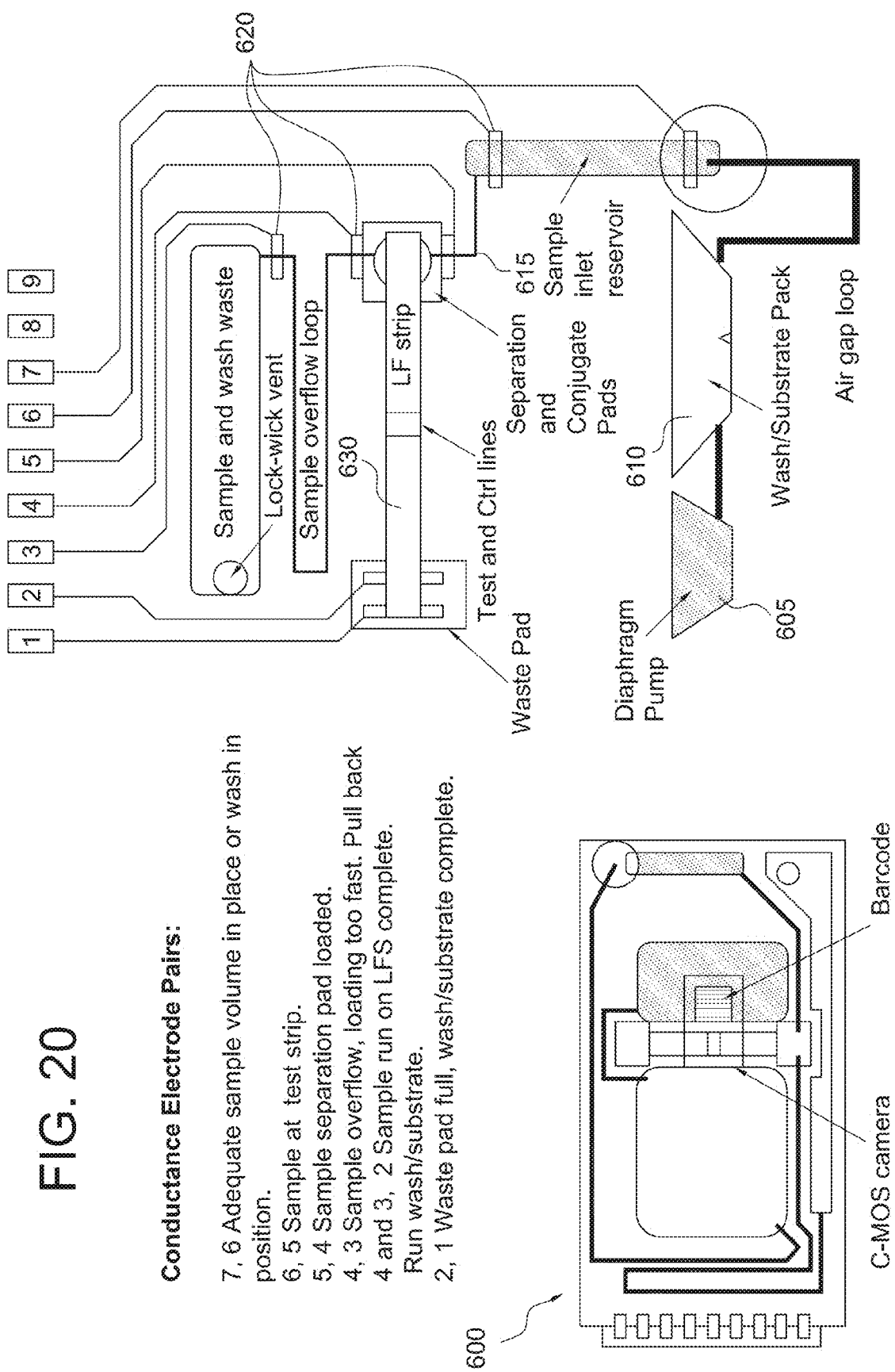
FIG. 20 shows a lateral flow strip cartridge with impedance detection and fluid position tracking.
Figure 21:
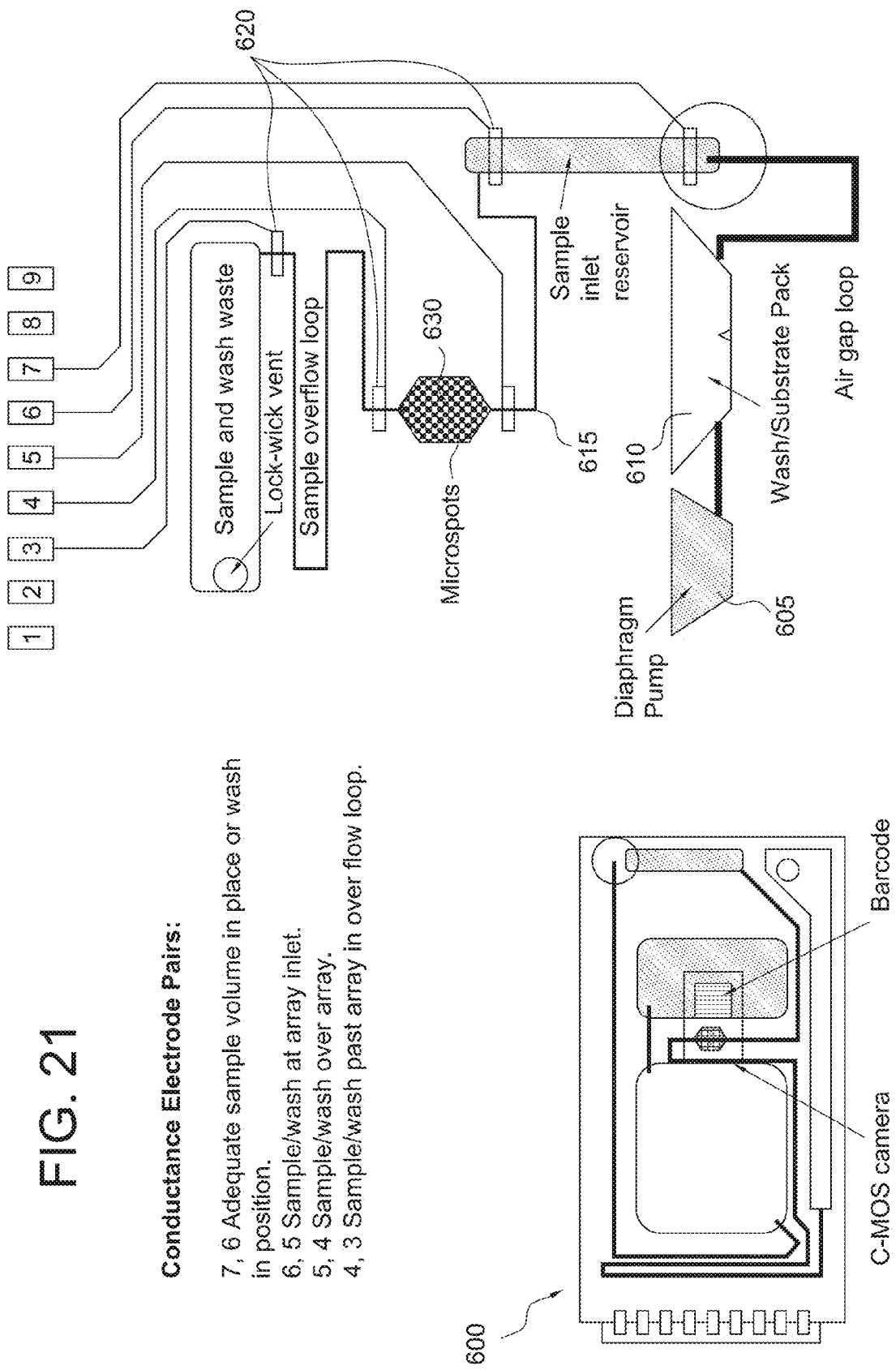
FIG. 21 shows a microspot array cartridge with impedance detection and fluid position tracking.

FIGS. 20 and 21 provide two examples (e.g., lateral flow and microspot array, respectively) for implementing conductance-based determination and active lateral flow movement in a cartridge test system. In accordance with some embodiments of the invention, the cartridge 600 may comprise a pump 605, a fluid-containing reservoir 610, a microfluidic circuit 615 with electrodes 620 at position control points, a lateral flow (chromatographic) test strip or a flow-through microspot assay chamber 630, and an imager, e.g., a camera chip or photosensor, for recording the assay using optical measurement.

In alternative embodiments, the position and/or total volume of the fluid can be determined by using the imager or an imaging sensor. For example, the sample fluid channels can be formed to route the fluid to the imaging area (as discussed above with respect to FIGS. 14 and 17A/B) for subsequent imaging by the imager and the determination of positioning within the microfluidic circuit. Specifically, the fluid may be imaged as it passes through the imaging area, which allows a precise determination of the timing of the fluid motion. One of ordinary skill in the art would understand that other means for detection may be utilized in the above-disclosed systems, e.g., amperometric-based determination may also be used for detecting the position of the fluid.

Cartridge with Combined Pneumatic and Lateral Flow Fluidic Features

In some embodiments, the invention relates to cartridges, as described above, that further comprise pneumatic fluidic actuation to provide a further degree of control over the various steps of the assays, e.g., the processes described with respect to the lateral flow device in FIG. 14 or 17A/B. As discussed above, the lateral flow test strips generally operate in a passive mode (i.e., the sample flows through a support matrix of the wick via capillary action). Due to the nature of passive systems, however, there is limited or no control over the time domain as the fluid or sample passes through the wick. Consequently there is limited or no control over the amount of mixing that may occur between the sample and the conjugate or bound antibodies in the capture zone. Therefore, in some embodiments, a pump, as described above, may be used with the cartridges to actively control fluid migration through an immuno-chromatographic assay. For example, the cartridge may comprise a displacement device, e.g., an air bladder, that is actuated by a pump to mix the sample with the conjugate and antibodies of the capture zone or control the time domain.

Figure 22:
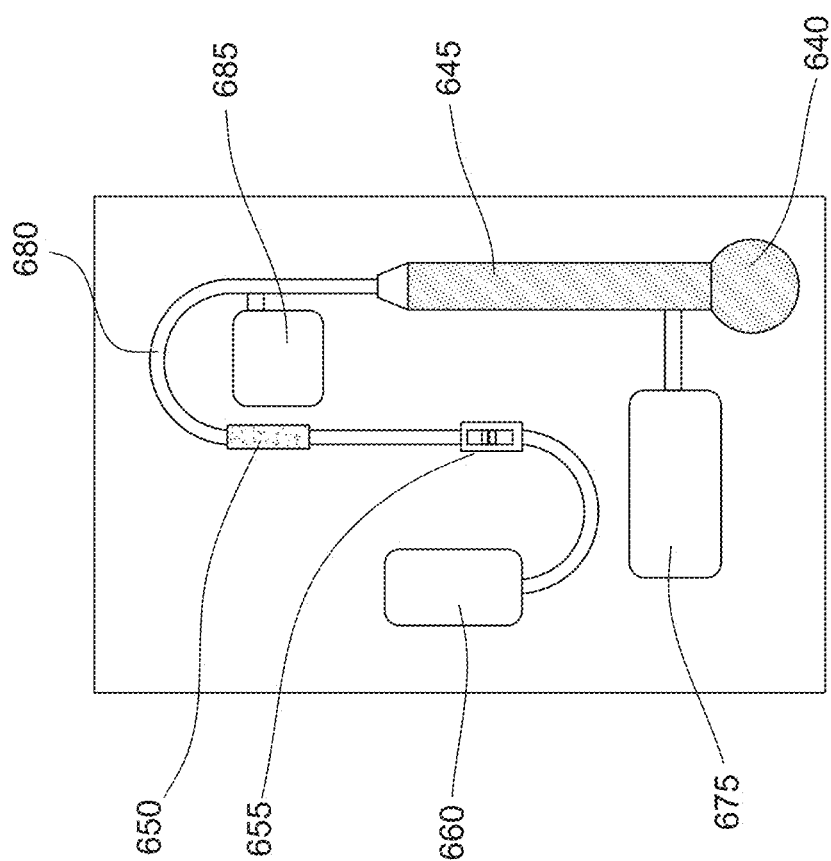
FIG. 22 shows a test device with pneumatic mixing of a labeled antibody with a sample further comprising a lateral flow capture zone.

FIG. 22 shows a design of an assay cartridge with a displacement device, e.g., an air bladder, and an immuno-chromatographic assay. One of ordinary skill in the art would understand that FIG. 22 does not represent a specific assay geometry, rather it represents a layout of elements that may be utilized in the cartridge for active fluid control, e.g., a test device with pneumatic mixing of a sample with a labeled antibody and a lateral flow capture zone. In some embodiments, the total sample volume may be between approximately 5 µL and 500 µL, thus the depicted sample chamber would accommodate such volumes in practical embodiments, and the adjoining conduits would be suitably sized.

As shown in FIG. 22, the cartridge comprises an inlet port 640 that is used to collect the sample. The sample may be provided, for example, in the form of urine, serum, plasma, or whole blood. The cartridge further comprises a sample fill chamber 645, a labeling zone 650, a chromatographic assay capture zone 655, a waste chamber 660, an air bladder 675, and fluidic channels 680 that provide a fluid connection between the various components of the cartridge. First, the cartridge is inserted into a reader, e.g., through the universal cartridge receiving port. The chromatographic assay capture zone is then imaged by an imager chip, e.g., a 2D barcode reader, and the air bladder 675 is actuated by a pump, e.g., a pneumatic pump, a hydraulic pump, a syringe, or the like. In some embodiments, the barcode reader and the pump may be controlled by embedded software within the reader, e.g., the computing device 215.

In operation, once the cartridge is inserted through receiving port, the sample accumulates in the sample fill chamber 645. A restriction, optionally a capillary stop, located at the end of the fill chamber 645 may provide an indication when the fluid level is sufficient. After the sample fluid is deposited in the cartridge, a latch (not shown) may be used to close the port. Once the latch is closed, the cartridge is inserted in the reader and an automated measurement cycle begins. The measurement cycle may be comprised of several phases. First, the air bladder 675 is activated to push the sample fluid to a labeling zone 650 where the sample comes into contact with an analyte-specific antibody conjugate, which preferably has been printed in a soluble form onto the walls of labeling zone 650. This dissolves the antibody into the sample and allows for binding of the analyte-specific antibody conjugate with the analyte. The air bladder 675 is then actuated to sequentially push and pull the fluid sample through the fluidic channels 680 on the cartridge. The resulting oscillatory motion facilitates mixing of the sample fluid with the antibody conjugate. Once the sample fluid has been satisfactorily mixed with the antibody conjugate, the air bladder 675 is actuated to push the fluid to the chromatographic assay capture zone 655 where the analyte-specific antibodies are immobilized to the chromatographic medium (e.g., a porous plug made of paper, nitrocellulose, etc.). The timing of these steps may be controlled by the software described with respect to FIG. 2. In some embodiments, completion of all the steps may take approximately two to twenty minutes depending on the assay and sample type.

Upon reaching the capture zone 655, any analyte present in the sample, now labeled with conjugate, will be immobilized by virtue of the capture antibodies resulting in localization of the labeled antigen at the capture zone. Optionally, the air bladder 675 can be actuated to sequentially push and pull the sample fluid across the capture zone 655 to ensure optimal capture of the antibodies. Once the analyte has been satisfactorily captured, the air bladder 675 can be optionally actuated to push the sample fluid into the waste chamber 660, leaving behind the captured antibodies. In some embodiments, a wash fluid contained within a wash fluid chamber 685 may be pushed through the chromatographic assay capture zone 655 to flush away components of the sample fluid that are not necessary for result generation or can be a source of interference, e.g., red blood cells. The wash fluid is preferably located in a rupturable pouch within the device. See, e.g., Lauks et al., U.S. Pat. No. 5,096,669, the entirety of which is incorporated herein by reference.

For detection of the labeled antigen, an illumination source and an imager located in the reader are activated, and one or more images are acquired of the chromatographic assay capture zone 655 and optionally an adjacent area comprising a barcode. The image or series of images are analyzed by the reader, e.g., the computing device 215. An automated software analysis derives a positive or negative result based on the characteristics of the acquired image or series of images. In some embodiments, the barcode may contain assay information, e.g., test identification, calibration data, color references, test cycle control parameter, expiration data and the like. Once the image acquisition is completed, the cartridge may be released from the instrument and disposed.

This embodiment has significant advantages over passive lateral flow immuno-chromatographic devices. For example, it enables instrument data capture of the test results, which are then available for transmission to a Laboratory Information System (LIS) or a Hospital Information System (HIS) for recordkeeping and billing.

The present embodiment also advantageously minimizes the time it takes to perform the test and reduces the opportunity for a user-induced error. For tests that are performed manually on typical lateral flow devices, a guideline for wait time after application of the sample on the wicking element before reading the assay is provided by the manufacturer. The wait time includes the time for capillary flow of the sample along the wicking element, the sample labeling time and the conjugate label capture time onto the area where the measurement is performed. For most tests currently commercially available, a wait time between several seconds and several minutes is typical. By using active fluid control, the present embodiment reduces the transit times from sample collection to the labeling zone and from the labeling zone to the capture zone. In addition to reducing the labeling and capture times when compared to passive capillary flow methods, active fluid mixing advantageously improves sensitivity.

This embodiment further allows customizing the measurement cycle for the fluid sample type. For example a β-hCG assay is compatible with both whole blood and urine samples. Labeling and capture phases of the measurement cycle can be optimized depending on the sample type by means of the active fluidic control. Such optimization is not typically possible for traditional lateral flow assays where assay completion times typically vary depending on the sample type and are based on compromises regarding the porosity and other properties of the lateral flow matrix. Further, imaging of the capture zone may optionally be performed at various times during the test cycle, resulting in a series of time resolved images. Analysis of the images may be conducted by the analysis software to derive the rate of color change in the capture region. From the knowledge of the rate of the change from controlled experiments during manufacture, the reader may be programmed with an anticipated completion time window for data collection for each sample type, blood, plasma, serum, urine etc. This adaptive data acquisition can lead to shorter measurement cycles.

Figure 23:
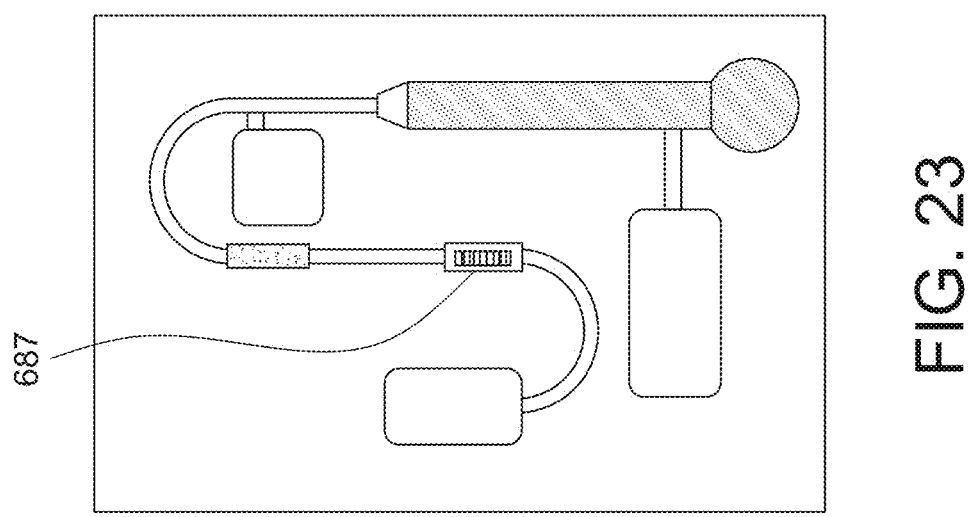
FIG. 23 shows a test device with pneumatic mixing of a labeled antibody with a sample further comprising multiple lateral flow capture zones.
Figure 24:
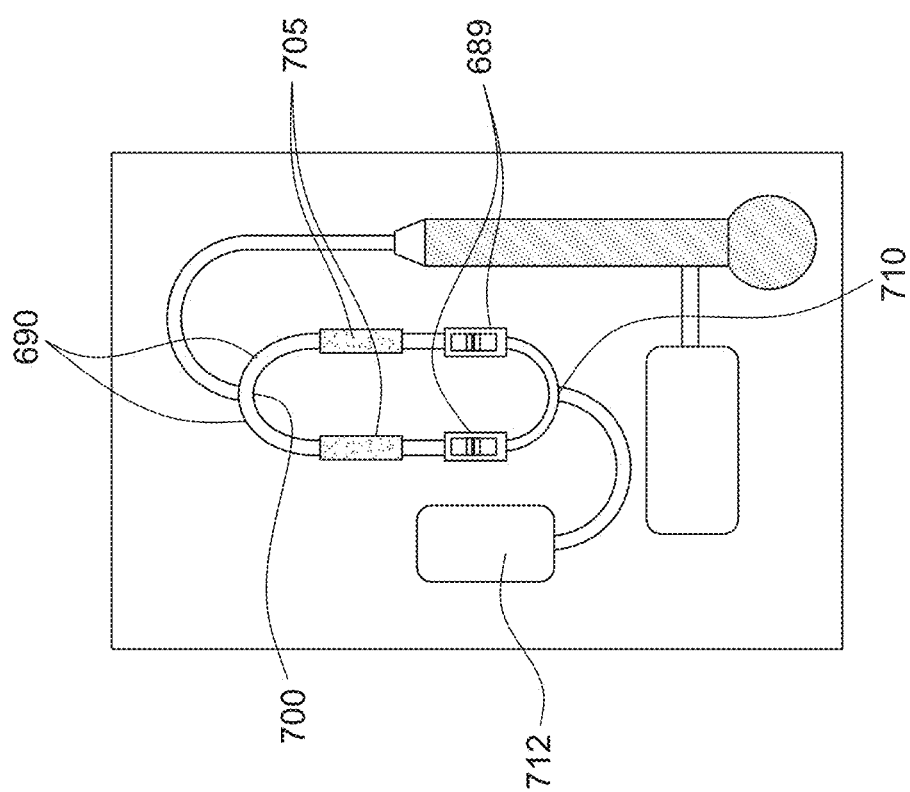
FIG. 24 shows another embodiment of a test device with pneumatic mixing of a labeled antibody with a sample further comprising lateral flow capture zones in multiple channels.

FIG. 23 shows another embodiment of a test device with pneumatic mixing of a labeled antibody with a sample further comprising multiple lateral flow capture zones 687. The present embodiment may also comprise multiplex assays. FIG. 24 shows an alternative embodiment of a test device with pneumatic mixing of a labeled antibody with a sample further comprising lateral flow capture zones 689 in multiple channels 690. Active fluidic control is extended to multiple labeling and chromatographic assay capture zones for a multiplexed assay of the same fluid sample. FIG. 24 further shows a manifold 700 that separates the sample fluid into two separate labeling zones 705. Another manifold 710 collects the sample fluid after detection in the capture chamber and allows disposal of the sample fluid in the waste chamber 712. This design can be extended to any number of channels that can practically fit on a cartridge and any number of capture zones that can be imaged by the imager, e.g., a barcode reader, within the reader.

The immuno-chromatographic assay cartridge may also incorporate multiple labeling and chromatographic assay capture zones in parallel. In this embodiment, the cartridge comprises a single labeling chamber where multiple analyte-specific antibody conjugates are printed in a dissolvable form. When the fluid sample comes in contact with the antibody conjugates they dissolve and the analytes of interest become labeled with their specific conjugate. The labeled analytes are then pushed to the chromatographic assay capture chamber by the pneumatic pump assembly. The capture chamber features multiple chromatographic assay capture zones sequentially arranged in the direction of the flow. Each analyte, now labeled with the conjugate, is immobilized to a specific area of the chromatographic medium.

In another embodiment, the cartridge layouts described above may include additional fluidic channels for delivering the fluid sample to other types of sensors. The other sensors are not limited to electrochemical sensors, but can include fiber optic sensors, waveguide sensors, surface acoustic wave sensors, surface plasmon wave sensors, thermal sensors and the like, for measuring designated sample properties. FIG. 25 shows this embodiment of the test device with pneumatic mixing of a labeled antibody with a sample further comprising lateral flow capture zones 720 in one channel and electrochemical detectors 725 in another channel. In this embodiment, the fluidic path is divided into two distinct paths. One path delivers the sample to the labeling and capture zones. The other path delivers the sample to an electrochemical sensors area. In this embodiment, the reader comprises an electrical connector, as discussed above with respect to FIGS. 3A-3D, for engaging the electrochemical sensors with the control circuitry within the reader.

Test Sample Separator

Figure 26:
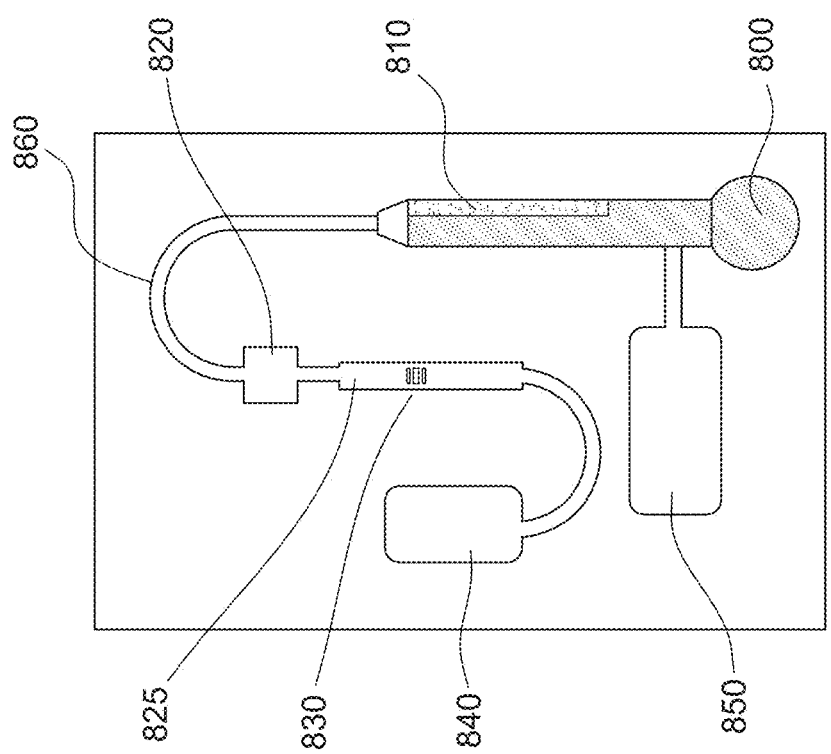
FIG. 26 shows a test device comprising a test sample separator in accordance with aspects of the invention.
Figure 27B:
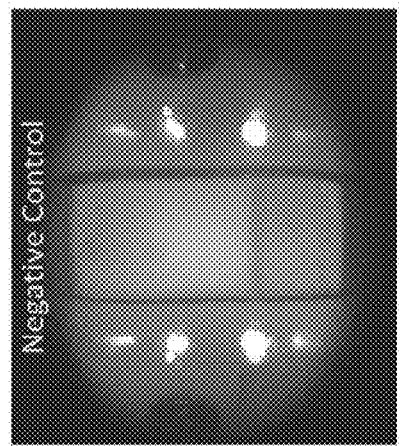
FIGS. 27A-27D show developed images for various concentrations of analyte.
Figure 27D:
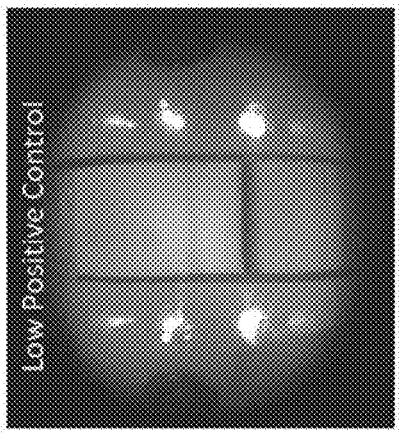
Figure 27A:
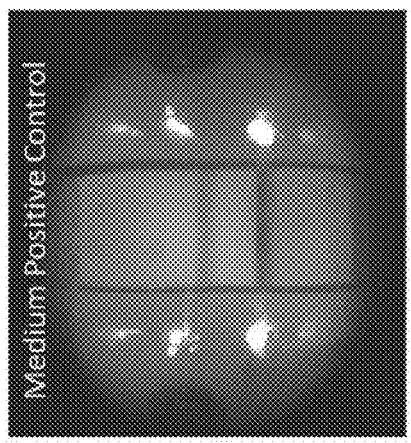
Figure 27C:
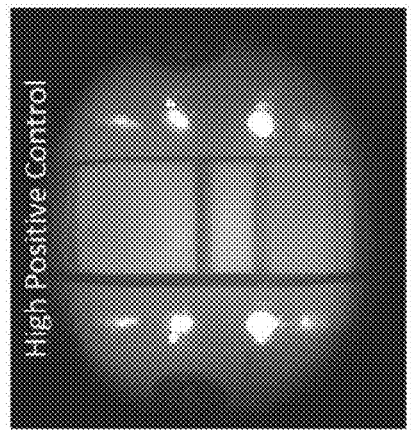

In some embodiments, cells or particles within a test sample may interfere with the flow of a sample through the wicking matrix of a lateral flow device. Therefore, the above-described cartridges may comprise a sample separator to separate the test sample, e.g., blood may be separated into cells and plasma. FIG. 26 shows a cartridge or device comprising a sample separator. The sample separator may comprise a separation chamber that utilizes gravity to assist in separation of the test sample. One of ordinary skill in the art would understand that FIG. 26 does not represent a specific geometry; rather it represents a concept of the elements found in the cartridge.

As shown in FIG. 26, the cartridge may comprise an inlet port 800 that is used to collect a test sample. In the case of the β-hCG assay, urine, plasma/serum, or whole blood can be used. The cartridge further comprises a sample fill chamber 810 that serves as a labeling zone, a sedimentation chamber 820, a lateral flow assay strip 825 with a chromatographic assay capture zone 830, a waste chamber 840, an air bladder 850, and fluidics channels 860 to connect the components of the cartridge. Once inserted in the reader, the chromatographic assay capture zone 830 can be imaged by an internal imager and the air bladder 850 can be actuated by a pump. Both the imager and the pump may be controlled by embedded software in the reader.

Once the sample is inserted through the inlet port 800, the biological sample accumulates in the sample fill chamber 810 and comes in contact with labeling conjugates already printed in the chamber 810. The conjugates dissolve in the sample fluid and the analyte of interest becomes labeled. Subsequently, the air bladder 850 may be activated to push the labeled sample fluid to a sedimentation chamber 820 where the sample, e.g., blood, is allowed to rest and sediment. Sedimentation can naturally happen by gravity or can be accelerated by a chemical process (e.g., addition of a clumping agent). The geometry of the chamber can be optimized to retain clumped blood cells while allowing the serum to continue flowing. During the period of time used for sedimentation, the orientation and motion of the reader is monitored by an internal accelerometer to ensure no unwanted motion perturbs the sedimentation process. Inertial forces due to unwanted motion or excessive angle orientation can prevent sedimentation at the bottom of the chamber.

Acceleration and angle deviation from gravity can be measured by a measuring device, e.g., Analog Devices ADXL345. The ADXL345 is a small, thin, ultra-low power, 3-axis accelerometer with high resolution (13-bit) measurement at up to ±16 g. The measuring device measures the static acceleration of gravity in tilt-sensing applications, as well as dynamic acceleration resulting from motion or shock. The ADXL345 high resolution (3.9 mg/LSB) enables measurement of inclination changes less than 1.0°. Threshold values can be assigned for both dynamic acceleration and angle deviation from rest position during the sedimentation phase of the test. If the accelerometer detects values for dynamic acceleration or angle that exceed threshold values, a computer in the reader, e.g., computing device 215 (discussed below), can take a series of actions that can include displaying a warning message to the operator, modifying the test cycle accordingly (e.g., additional rest time), correcting the measurement value or issuing an error code and canceling the test altogether.

The air bladder 850 is further activated to push the labeled and separated sample fluid to a sample application zone on the lateral flow assay strip 825. Once the labeled and separated sample fluid comes into contact with the application zone on the lateral flow assay strip, capillary forces pull the fluid toward the chromatographic assay capture zone 830 where the analyte-specific antibodies are immobilized to the chromatographic medium. Upon reaching the capture zone 830, any analyte present in the sample, now labeled with conjugate, will be immobilized by virtue of the capture antibodies resulting in localization/concentration of the labeled antigen at the capture zone 830.

Illumination sources and an imager (e.g., located in the reader) are controlled to acquire one or several images of the chromatographic assay capture zone 830. The image or the series of images are analyzed by the software of the reader. An automated software analysis derives a positive or negative result based on the characteristics of the acquired image or series of images. Once the image acquisition is completed, the cartridge may be released and disposed.

Although the embodiment of a sample separator has been described within the context of a lateral flow assay to allow sedimentation of the blood cells in a dedicated part of the fluidic channels, the concept of monitoring the angle and dynamic motion of the reader during test with an internal sensor (e.g., multi-axis accelerometer such as the ADXL345 or other) is applicable to any assay (e.g., electro-chemical or optical) that can benefit from stability requirements. Generally, if a stability requirement exists as part of a testing cycle on a cartridge, a dynamic motion or angle sensor can be activated to measure motion and position parameters during the critical phases of the measurement cycle. If unacceptable motion is detected, an internal logic can modify the testing cycle accordingly or initiate a warning communication to the user or both.

System Environment

In view of the foregoing, it will be appreciated by those of ordinary skill in the art that in some aspects the present invention is embodied in a single device or apparatus (e.g., a reader device or a test cartridge), a system, a method or a computer program product. Accordingly, in some embodiments, the present invention relates to certain hardware, software (including firmware, resident software, microcode, etc.) or embodiments combining software and hardware, which may be referred to herein as a "circuit," "module" or "system." Furthermore, in some embodiment, the present invention may take the form of a computer program product embodied in one or more computer readable medium(s) having computer readable program code embodied thereon. For example, such software, systems and computer readable medium(s) may be incorporated into the reader device or test cartridges of the invention.

Any combination of one or more computer readable medium(s) may be utilized. The computer readable medium may be a computer readable signal medium or a computer readable storage medium. A computer readable storage medium may be, for example, but is not limited to, an electronic, magnetic, optical, electromagnetic, infrared, or semiconductor system, apparatus, or device, or any suitable combination of the foregoing. A non-limiting list of specific examples of the computer readable storage medium includes: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device, e.g., a reader device or a cartridge.

A computer readable signal medium may include, for example, a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer usable storage memory can be any physical storage device such as random access memory (RAM) or a read-only memory (ROM) to name a few examples.

Program code embodied on a computer readable medium may be transmitted using any appropriate medium, including but not limited to wireless, wireline, optical fiber cable, RF, etc., or any suitable combination of the foregoing.

Computer program instructions may also be stored in the computer readable medium that can direct a computer, other programmable data processing apparatus, or other devices to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 2:
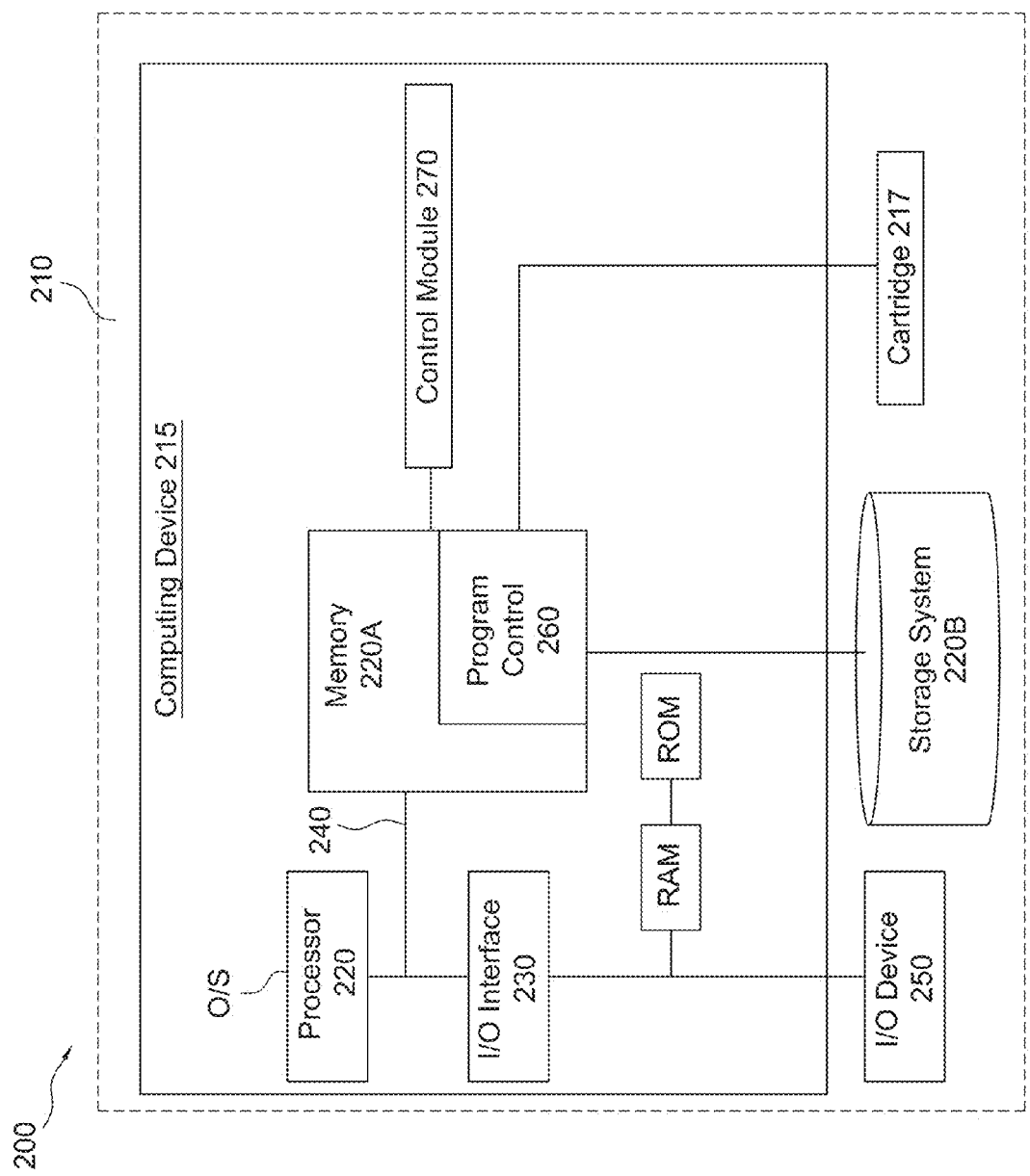
FIG. 2 is an illustrative external environment for implementing the invention in accordance with some embodiments of the invention.

FIG. 2 shows an illustrative environment 200 for managing the processes in accordance with some embodiments of the invention. To this extent, the environment 200 includes a server or other computing system 210 that can perform the processes described herein. In particular, the computing system 210 includes a computing device 215 such as a cartridge reader device and a cartridge 217 (e.g., a cartridge comprising optical and/or electrochemical assay systems). An example of such a system is the aforementioned i-STAT system sold by Abbott Point of Care Inc. The i-STAT portable blood analysis system may comprise a Wi-Fi-enabled reader device that works in conjunction with single-use blood testing cartridges that contain sensors for various analytes. The computing device 215 can be resident on a network infrastructure or computing device of a third party service provider (any of which is generally represented in FIG. 2).

The computing device 215 also includes a processor 220, memory 220A, an I/O interface 230, and a bus 240. The memory 220A can include local memory employed during actual execution of program code, bulk storage, and cache memories which provide temporary storage of at least some program code in order to reduce the number of times code should be retrieved from bulk storage during execution. In addition, the computing device includes RAM, ROM, and an operating system (O/S).

The computing device 215 may be in communication with an external I/O device/resource 250 and an external storage system 220B. For example, the I/O device 250 can comprise any device that enables an individual to interact with the computing device 215 (e.g., user interface) or any device that enables the computing device 215 to communicate with one or more other computing devices using any type of communications link. The external I/O device/resource 250 may be for example, a handheld device, PDA, handset, keyboard, etc.

In general, the processor 220 executes computer program code (e.g., program control 260), which can be stored in the memory 220A and/or storage system 220B. Moreover, in accordance with some aspects of the invention, the program control 260 controls at least one control and/or measurement module 270 to perform the processes described herein. The control module and/or measurement 270 can be implemented as one or more program code in the program control 260 stored in memory 220A as separate or combined modules. Additionally, the control and/or measurement module 270 may be implemented as separate dedicated processors or a single or several processors to provide the function of this tool. While executing the computer program code, the processor 220 can read and/or write data to/from memory 220A, storage system 220B, and/or I/O interface 250. The program code executes the processes of the invention. The bus 240 provides a communications link between each of the components in the computing device 215.

In some embodiments, the control and/or measurement module 270 may perform optical and/or electrochemical tests in conjunction with the cartridge 217 comprising optical and/or electrochemical assay systems. For example, in accordance with some aspects of the invention, the control and/or measurement module 270 can operate sensors of the optical and/or electrochemical assay systems within the cartridge 217 to provide qualitative, semi-quantitative, and/or quantitative measurements of an analyte within a test sample, and display such measurements to a user. In another embodiment, upon insertion of a cartridge 217 device into the reader device, the control and/or measurement module 270 may operate one or more feature of the reader device to determine whether the cartridge 217 is an optical cartridge, an electrochemical cartridge, or both.

EXAMPLE

The present invention may be better understood in view of the following non-limiting example.

A series of experiments were conducted to determine the ability of the optical detection method to quantify analyte concentrations. Biological samples consisting of male urine spiked with β-hCG at various concentrations were used on lateral flow assay strips designed to indicate a response when the analyte concentration exceeds 25 mIU/mL. Images were collected during the experiments and processed to produce a difference image and signal. FIGS. 27A-D depict images of the developed assay strips at 0, 15, 100 and 1000 mIU/mL of β-hCG. The bar graph located below each image indicates the concentration of analyte compared to the qualitative detection threshold of the lateral flow assays. The triangle indicates the level for which the lateral flow assay strips are designed to indicate a positive result. Wet-up images were obtained for each experiment and used to create a difference image and signal. FIGS. 28A-D depict the processed images that were obtained by subtracting the images taken after development from the images taken during wet-up. FIGS. 29A-D depict corresponding graphical plots when the pixel values are integrated across the highlighted rectangular area.

FIG. 29A shows the 2-D graphical plot for the case where there is no β-hCG in the sample. Only one peak is visible on the plot. The visible peak corresponds to the control band. FIG. 29B shows the graphical plot of pixel intensity for the case where the sample had a known concentration of 15 mIU/mL. Two peaks are visible on the plot. The larger peak corresponds to the control band. The smaller one corresponds to the capture zone of the analyte. FIG. 29C shows the case where the sample had a known concentration of 100 mIU/mL. Two peaks are visible on the plot. The larger peak corresponds to the control band. The smaller peak corresponds to the capture zone of the analyte. Note that the relative size of the two peaks is different when the analyte concentrations are different. Specifically, the peak corresponding to the analyte capture zone gets larger as the concentration increases. FIG. 29D corresponds to the case where the analyte concentration is 1000 mIU/mL. Two peaks are still visible as was the case with the analyte concentrations shown in FIGS. 29B and 29C. However, in FIG. 29D where the analyte concentration is 1000 mIU/mL, the peak corresponding to the capture zone has become larger than the peak corresponding to the control band. Specifically, it is typical for the intensity of the capture zones to become larger than the control zones when the analyte concentration becomes very high.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

We claim:

1. An instrument comprising:
    a housing including a cartridge receiving port configured to receive a plurality of testing cartridges, wherein said plurality of testing cartridges comprises at least two selected from the group consisting of: a qualitative or semi-quantitative lateral flow test device; a quantitative non-lateral flow test device; and a combined qualitative or semi-quantitative lateral flow test device and a quantitative non-lateral flow test device;
    an optical sensor within said port configured to read a first signal from an optical feature of said qualitative or semi-quantitative lateral flow test device or said combined qualitative or semi-quantitative lateral flow test device and a quantitative non-lateral flow test device; and
    an electrical connector within said port configured to mate with one or more electrodes of said quantitative non-lateral flow test device or said combined qualitative or semi-quantitative lateral flow test device and a quantitative non-lateral flow test device.

2. The instrument of claim 1, wherein said qualitative or semi-quantitative lateral flow test device or said combined qualitative or semi-quantitative lateral flow test device and said quantitative non-lateral flow test device comprises a testing system operable to detect an analyte selected from the group consisting of: hCG and drugs of abuse.

3. The instrument of claim 1, wherein said quantitative non-lateral flow test device or said combined qualitative or semi-quantitative lateral flow test device and said quantitative non-lateral flow test device comprises a testing system operable to detect an analyte selected from the group consisting of: hCG, K, Na, Cl, Ca, Mg, pH, pO2, pCO2, glucose, urea, creatinine, lactate, CKMB, TnI, TnT, BNP, NTproBNP, proBNP, TSH, D-dimer, PSA, PTH, NGAL, galectin-3, AST, ALT, albumin, phosphate and ALP.

4. The instrument of claim 1, wherein said qualitative or semi-quantitative lateral flow test device; said quantitative non-lateral flow test device; and said combined qualitative or semi-quantitative lateral flow test device and a quantitative non-lateral flow test device are configured to test for a predetermined analyte in a biological sample selected from the group consisting of: urine, blood, plasma, serum, and amended forms thereof.

5. An analyte testing system comprising:
- a plurality of testing cartridges including at least two selected from the group consisting of: a qualitative or semi-quantitative lateral flow test device; a quantitative non-lateral flow test device; and a combined qualitative or semi-quantitative lateral flow test device and a quantitative non-lateral flow test device; and
- an instrument including:
  - a housing with a cartridge receiving port configured to receive said plurality of testing cartridges;
  - a first detector comprising an electrical connector configured to connect to a quantitative electrochemical sensor in at least one of said plurality of testing cartridges; and
  - a second detector comprising an optical imager configured to image an optical assay in at least one of said plurality of testing cartridges.

6. The instrument of claim 5, wherein said qualitative or semi-quantitative lateral flow test device or said combined qualitative or semi-quantitative lateral flow test device and said quantitative non-lateral flow test device comprises a testing system operable to detect an analyte selected from the group consisting of: hCG and drugs of abuse.

7. The instrument of claim 5, wherein said quantitative non-lateral flow test device or said combined qualitative or semi-quantitative lateral flow test device and said quantitative non-lateral flow test device comprises a testing system operable to detect an analyte selected from the group consisting of: hCG, K, Na, Cl, Ca, Mg, pH, pO2, pCO2, glucose, urea, creatinine, lactate, CKMB, TnI, TnT, BNP, NTproBNP, proBNP, TSH, D-dimer, PSA, PTH, NGAL, galectin-3, AST, ALT, albumin, phosphate and ALP.

8. The instrument of claim 5, wherein said qualitative or semi-quantitative lateral flow test device; said quantitative non-lateral flow test device; and said combined qualitative or semi-quantitative lateral flow test device and a quantitative non-lateral flow test device are configured to test for a predetermined analyte in a biological sample selected from the group consisting of: urine, blood, plasma, serum, and amended forms thereof.

9. An instrument comprising: a connector configured to mate with electrical contacts of at least two test devices selected from the group consisting of: a qualitative or semi-quantitative lateral flow test device; a quantitative non-lateral flow test device; and a combined qualitative or semi-quantitative lateral flow test device and a quantitative non-lateral flow test device; and
- an imager configured to image a detection zone on a lateral flow test strip on the qualitative or semi-quantitative lateral flow test device or said combined qualitative or semi-quantitative lateral flow test device and the quantitative non-lateral flow test device.

10. The instrument of claim 9, wherein said imager is further configured to image a two-dimensional barcode adjacent said detection zone on said qualitative or semi-quantitative lateral flow test device or said combined qualitative or semi-quantitative lateral flow test device and the quantitative non-lateral flow test device.

11. The instrument of claim 10, wherein the imager is further configured to image said two-dimensional barcode and said detection zone at a same time.

12. The instrument of claim 11, wherein said electrical contacts are connected to a quantitative electrochemical sensor in said quantitative non-lateral flow test device or said combined qualitative or semi-quantitative lateral flow test device and the quantitative non-lateral flow test device.

* * * * *